United States Patent [19]

Bomhard et al.

[11] Patent Number: 4,912,115

[45] Date of Patent: Mar. 27, 1990

[54] HETEROAROMATIC AMINE DERIVATIVES, PHARMACEUTICAL COMPOSITIONS CONTAINING THESE COMPOUNDS AND PROCESSES FOR PREPARING THEM

[75] Inventors: Andreas Bomhard, Biberach; Joachim Heider, Warthausen; Manfred Psiorz, Biberach; Norbert Hauel, Biberach; Berthold Narr, Biberach; Klaus Noll, Warthausen, all of Fed. Rep. of Germany; Christian Lillie; Walter Kobinger, both of Vienna, Austria; Willi Diederen, Biberach, Fed. Rep. of Germany

[73] Assignee: Dr. Karl Thomae GmbH, Biberach an der Riss, Fed. Rep. of Germany

[21] Appl. No.: 125,626

[22] Filed: Nov. 25, 1987

[30] Foreign Application Priority Data

Nov. 28, 1986 [DE] Fed. Rep. of Germany ....... 3640641

[51] Int. Cl.[4] ...................... A61K 31/47; C07D 409/12
[52] U.S. Cl. ....................................... 514/309; 546/141
[58] Field of Search ........................ 546/141; 514/309

[56] References Cited

U.S. PATENT DOCUMENTS 4,118,494 10/1978 Kuntsmann et al. ............... 514/309
4,137,318 1/1979 Eberlein et al. ...................... 546/141
4,375,471 3/1983 Effland et al. ....................... 514/309

Primary Examiner—Mary C. Lee
Assistant Examiner—Joseph McKane
Attorney, Agent, or Firm—David E. Frankhouser; Mary-Ellen M. Timbers; Alan R. Stempel

[57] ABSTRACT

The present invention relates to new heteroaromatic amine derivatives of general formula

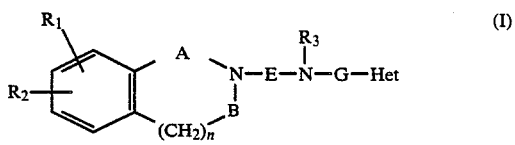

wherein the substituents are defined hereinbelow, which have valuable pharmacological properties, particularly a heart rate lowering activity and a positive inotropic activity.

12 Claims, No Drawings

HETEROAROMATIC AMINE DERIVATIVES, PHARMACEUTICAL COMPOSITIONS CONTAINING THESE COMPOUNDS AND PROCESSES FOR PREPARING THEM

The present invention relates to new heteroaromatic amine derivatives of general formula $$R_1\text{-}\underset{R_2}{\diagdown}\text{Ar}\diagup\underset{(CH_2)_n}{\overset{A}{\diagdown}}N\text{-}E\text{-}\underset{B}{\overset{R_3}{N}}\text{-}G\text{-}Het \qquad (I)$$

the N-oxides thereof and, if the compounds contain an optically active carbon atom, the enantiomers and acid addition salts thereof, particularly, for pharmaceutical use, the physiologically acceptable acid addition salts thereof with inorganic or organic acids, processes for preparing them and pharmaceutical compositions containing these compounds.

The new compounds have valuable pharmacological properties, particularly a heart rate lowering activity and the effect of reducing the $O_2$ requirements of the heart, as well as a mild hypotensive activity and a positive inotropic activity.

In general formula I above, n is the number 0 or 1,

A is a methylene, carbonyl or thiocarbonyl group,

B is a methylene, carbonyl or thiocarbonyl group, whilst only one of the groups A or B may represent a thiocarbonyl group and in this case the other group A or B must represent a methylene group, E represents a straight-chained alkylene group with 2 to 4 carbon atoms optionally substituted by an alkyl group with 1 to 3 carbon atoms, G represents a straight-chained alkylene group with 1 to 6 carbon atoms optionally substituted by an alkyl group with 1 to 3 carbon atoms, $R_1$ and $R_2$, which may be identical or different, represent hydrogen atoms, alkyl or alkoxy groups each having 1 to 3 carbons atoms in each alkyl moiety or $R_1$ and $R_2$ together represent an alkylenedioxy group with 1 to 2 carbon atoms, $R_3$ represents a hydrogen atom, an alkenyl group with 3 to 5 carbon atoms, an alkyl or phenylalkyl group, wherein the alkyl moiety may contain from 1 to 3 carbon atoms, and Het represents a 5- or 6-membered heteroaromatic ring bound via a carbon or nitrogen atom and containing an oxygen, sulphur or nitrogen atom, two nitrogen atoms or one nitrogen atom and one oxygen or sulphur atom, whilst this ring may additionally be bound via two adjacent carbon atoms to a 1,3-propylene, 1,4-butylene or 1,4-buta-1,3-dienylene group, and in this case the bonding may be effected via the carbon ring, whilst the carbon structure of the above-mentioned aromatic and heteroaromatic rings may be mono- or disubstituted by a halogen atom or by an alkyl, hydroxy, alkoxy, phenylalkoxy, phenyl, dimethoxyphenyl, nitro, amino, acetylamino, carbamoylamino, N-alkyl-carbamoylamino, hydroxymethyl, mercapto, alkylmercapto, alkylsulphinyl, alkylsulphonyl, alkylsulphonyloxy, alkylsulphonylamino, alkoxycarbonylmethoxy, carboxymethoxy or alkoxymethyl group or may be substituted by a methylenedioxy or ethylenedioxy group and at the same time any imino group present in the above-mentioned heteroaromatic groups may be substituted by an alkyl, phenylalkyl or phenyl group, and the above-mentioned alkyl moieties may each contain from 1 to 3 carbon atoms.

As examples of the definitions of the groups given above, $R_1$ may represent a hydrogen atom, a methyl, ethyl, n-propyl, isopropyl, methoxy, ethoxy, n-propoxy or isopropoxy group, $R_2$ may represent a hydrogen atom, a methyl, ethyl, n-propyl, isopropyl, methoxy, ethoxy, n-propoxy or isopropoxy group or together with $R_1$ it may represent a methylenedioxy or ethylenedioxy group, $R_3$ may represent a hydrogen atom, a methyl, ethyl, n-propyl, isopropyl, benzyl, 1-phenylethyl, 2-phenylethyl, 1-phenylpropyl, 1-methyl-1-phenylethyl, 3-phenylpropyl, allyl, n-but-2-enyl or n-pent-2-enyl group, E may represent an ethylene, n-propylene, n-butylene, 1-methylethylene, 2-ethyl-ethylene, 1-propylethylene, 1-methyl-n-propylene, 2-methyl-n-propylene, 1-ethyl-n-propylene, 3-ethyl-n-propylene, 2-propyl-n-propylene, or 2-methyl-n-butylene group, G may represent a methylene, ethylidene, n-propylidene, n-butylidene, 2-methyl-propylidene, ethylene, 1-methyl-ethylene, 2-ethyl-ethylene, 1-propyl-ethylene, 2-methyl-ethylene, n-propylene, n-butylene, n-pentylene, n-hexylene, 1-methyl-n-propylene, 3-methyl-n-propylene, 1-methyl-n-butylene, 1-methyl-n-pentylene, 1-ethyl-n-propylene, 2-ethyl-n-propylene or 1-ethyl-n-butylene group and Het may represent a pyrrol-2-yl, pyrrol-3-yl, N-methyl-pyrrol-2-yl, N-methyl-pyrrol-3-yl, 1,2-dimethyl-pyrrol-3-yl, 2,5-dimethyl-pyrrol-3-yl, furan-2-yl, furan-3-yl, 5-methyl-furan-2-yl, 2-methyl-furan-3-yl, 5-nitro-furan-2-yl, 5-methyoxymethyl-furan-2-yl, benzo[b]furan-2-yl, benzo[b]furan-3-yl, 7-methyl-benzo[b]furan-3-yl, 2-methoxy-benzo[b]furan-3-yl, 3-methoxy-benzo[b]furan-2-yl, 4-methoxy-benzo[b]furan-3-yl, 5-methoxy-benzo[b]furan-3-yl, 6-methoxy-benzo[b]furan-3-yl, 7-methoxy-benzo[b]furan-3yl, 5-methoxy-3-phenyl-benzo[b]furan-2-yl, 3-methyl-5-methoxy-benzo[b]furan-2-yl, thien-2-yl, thien-3-yl, 5-methyl-thien-2-yl, 2-methyl-thien-3-yl, 3-methyl-thien-2-yl, 2,5-dimethyl-thien-3-yl, 4,5,6,7-tetrahydro-benzo[b]thien-3-yl, 4,5,6,7-tetrahydro-benzo[b]thien-2-yl, 5-chloro-thien-2-yl, 5-bromo-thien-2-yl, 5-phenyl-thien-2-yl, 2-phenyl-thien-3-yl, benzo[b]thien-2-yl, benzo[b]thien-3-yl, 2,5-dimethyl-benzo[b]thien-3-yl, 5-methyl-benzo[b]thien-3-yl, 6-methyl-benzo[b]thien-3-yl, 5-chloro-benzo[b]thien-2-yl, 5-bromo-benzo[b]thien-3-yl, 6-hydroxy-benzo[b]thien-3-yl, 7-hydroxy-benzo[b]thien-3-yl, 5-hydroxy-benzo[b]thien-2-yl, 6-hydroxy-benzo[b]- thien-2-yl, 7-hydroxy-benzo[b]thien-2-yl, 3-methoxy-benzo[b]thien-2-yl, 4-methoxy-benzo[b]thien-2-yl, 5-methoxy-benzo[b]thien-2-yl, 6-methoxy-benzo[b]thien-2-yl, 7-methoxy-benzo[b]thien-2-yl, 2-methoxy-benzo[b]thien-3-yl, benzo[b]thien-4-yl, benzo[b]thien-5-yl, benzo[b]thien-6-yl, benzo[b]thien-7-yl, 4-methoxy-benzo[b]thien-3-yl, 5-methoxy-benzo[b]thien-3-yl, 6-methoxy-benzo[b]thien-3-yl, 7-methoxy-benzo[b]thien-3-yl, 5,6-dimethoxy-benzo[b]- thien-3-yl, 5,6-methylenedioxy-benzo[b]thien-3-yl, 6-ethoxy-benzo[b]thien-3-yl, 6-n-propoxy-benzo[b]thien-3-yl, 6-isopropoxy-benzo[b]thien-3yl, 6-mercapto-benzo[b]- thien-3-yl, 6-methylmercapto-benzo[b]thien-3-yl, 6-methylsulphinylbenzo[b]thien-3-yl, 6-methylsulphonyl-benzo[b]thien-3-yl, 6- methylsulphonyloxy-benzo[b]thien-3-yl, 6-methoxycarbonylmethoxy-benzo[b]thien-3-yl, 6-ethoxycarbonylmethoxy-benzo[b]thien-3-yl, 6-carboxymethoxy-benzo[b]thien-3-yl, 6-amino-benzo[b]thien-3-yl, 6-methylamino-benzo[b]thien-3yl, 6-dimethylamino-benzo[b]thien-3-yl, 6-diethylamino-benzo[b]thien-3-yl, 6-acetamino-benzo[b]thien-3-yl, 6-methylsulphonylamino-benzo[b]thien-3-yl, pyrazol-1-yl, pyrazol-3-yl, 3,5-dimethyl-pyrazol-1-yl, 1,5-dimethyl-pyrazol-3-yl, imidazol-1-yl, imidazol-2-yl, imidazol-4(5)-yl, 1-methyl-imidazol-4-yl, 1-benzyl-imidazol-4-yl, 5-nitro-2-methyl-imidazol-1-yl, 2-(3,4-dimethoxy-phenyl)-imidazol-4(5)-yl, benzo[d]imidazol-1-yl, 2-benzyl-benzo[d]imidazol-1-yl, benzo[d]imidazol-2-yl, oxazol-4-yl, oxazol-5-yl, isoxazol-3-yl, 3-methyl-isoxazol-5-yl, 5-methyl-isoxazol-3-yl, 3,5-dimethyl-isoxazol-4-yl, 4-methyl-thiazol-5-yl, benzo[d]oxazol-2-yl, benzo[d]isoxazol-3-yl, benzo[d]thiazol-2-yl, 5-ethoxy-benzo[d]thiazol-2-yl, benzo[d]isothiazol-3-yl, benzo[d]pyrazol-1-yl, benzo[d]pyrazol-3-yl, pyridin-2-yl, pyridin-3-yl, pyridin-4-yl, pyridin-3-yl-N-oxide, 6-methyl-pyridin-2-yl, 4-nitro-pyridin-2-yl, 4-amino-pyridin-2-yl, 4-acetylamino-pyridin-2-yl, 4-carbamoylamino-pyridin-2-yl, 4-N-methyl-carbamoylamino-pyridin-2-yl, 2-chloro-pyridin-3-yl, 2-chloro-pyridin-4-yl, 6-chloro-pyridin-2-yl, 6-hydroxymethyl-pyridin-2-yl, indol-2-yl, indol-3-yl, 5-methoxy-indol-3-yl, 5-methyl-indol-3-yl, 7-methyl-indol-3-yl, 5-bromo-indol-3-yl, 5-benzyloxy-indol-3-yl, N-methyl-indol-3-yl, quinolin-2-yl, isoquinolin-1-yl, 2-methyl-quinolin-4-yl, 7-methyl-quinolin-2-yl, 4-chloro-quinolin-2-yl, 6,7-dimethoxy-quinolin-4-yl, 6,7-dimethoxy-isoquinolin-4-yl or 6,7-dimethoxy-isoquinolin-4-yl-N-oxide group.

The following compounds which are covered by the scope of the present invention may also be mentioned by way of example:

2-[N-methyl-N-(2-(thien-2-yl)-ethyl)-3-amino-propyl]-6, 7-dimethoxy-1-oxo-1,2,3,4-tetrahydro-isoquinoline 2-[N-methyl-N-(2-(indol-3-yl)-ethyl)-3-amino-propyl]-5, 6-dimethoxy-phthalimide 2-[N-methyl-N-(2-(thien-2-yl)-ethyl)-3-amino-propyl]-5, 6-dimethoxy-1,3-dihydro-1-oxo-isoindole 2-[N-methyl-N-(3-(pyridin-4-yl)-propyl)-3-amino-propyl]-6,7-methylenedioxy-1-oxo-1,2,3,4-tetrahydro-isoquinoline 2-[N-methyl-N-(3-(pyridin-4-yl)-propyl)-3-amino-propyl]-5,6-dimethyl-1,3-dihydro-isoindole 2-[N-methyl-N-(2(6,7-dimethoxy-isoquinolin-4-yl)-ethyl)-3-amino-propyl-6,7-dimethoxy-1-oxo-1,2,3,4-tetrahydro-isoquinoline 2-[N-methyl-N-(4-(thien-2-yl)-butyl)-3-amino-propyl]-6,7-dimethoxy-1-oxo-1,2,3,4-tetrahydro-isoquinoline 2-[N-methyl-N-(2-(benzo[b]furan-2-yl)-ethyl)-3-amino-propyl]-6,7-dimethoxy-1-oxo-1,2,3,4-tetrahydro-isoquinoline 2-[N-methyl-N-(2-(benzo[b]thien-3-yl)-ethyl)-3-amino-propyl]-6,7-dimethoxy-1-oxo-1,2,3,4-tetrahydro-isoquinoline 2-[N-methyl-N-(2-(thien-3-yl)-ethyl)-3-amino-propyl]-6,7-dimethoxy-1-oxo-1,2,3,4-tetrahydro-isoquinoline 2-[N-methyl-N-(2-(indol-3-yl)-ethyl)-3-amino-propyl]-6,7-dimethoxy-1-oxo-1,2,3,4-tetrahydro-isoquinoline 2-[N-methyl-N-(3-(indol-3-yl)-propyl)-3-amino-propyl]-6,7-dimethoxy-1-oxo-1,2,3,4-tetrahydro-isoquinoline 2-[N-methyl-N-(4-(thien-2-yl)-butyl)-3-amino-propyl]-5,6-dimethoxy-phthalimide 2-[N-methyl-N-(3-(indol-3-yl)-propyl)-3-amino-propyl]-5,6-dimethoxy-phthalimide 2-[N-methyl-N-(2-(thien-3-yl)-3-amino-propyl]-5,6-dimethoxy-phthalimide 2-[N-methyl-N-(2-(benzo[b]thien-3-yl)-ethyl)-3-amino-propyl]-5,6-dimethoxy-phthalimide 2-[N-methyl-N-(2-(thien-2-yl)-ethyl)-3-amino-propyl]-5,6-dimethoxy-phthalimide 2-[N-methyl-N-(3-(pyridin-3-yl)propyl)-3-amino-propyl]-6,7-dimethoxy-1-oxo-1,2,3,4-tetrahydro-isoquinoline 2-[N-methyl-N-(3-(pyridin-3-yl-N-oxide)-propyl)-3-amino-propyl]-6,7-dimethoxy-1-oxo-1,2,3,4-tetrahydro-isoquinoline 2-[N-methyl-N-(2-(indol-3-yl)-ethyl)-3-amino-propyl]-5,6-dimethoxy-1,3-dihydro-1-oxo-isoindole 2-[N-methyl-N-(3-(indol-3-yl)-propyl)-3-amino-propyl]-5,6-dimethoxy-1,3-dihydro-1-oxo-isoindole 2-[N-methyl-N-(2-(thien-3-yl)-ethyl)-3-amino-propyl]-5,6-dimethoxy-1,3-dihydro-1-oxo-isoindole 2-[N-methyl-N-(2-(benzo[b]thien-3-yl)-ethyl)-3-amino-propyl]-5,6-dimethoxy-1,3-dihydro-1-oxo-isoindole 2-[N-methyl-N-(3-(pyridin-4-yl)-propyl)-3-amino-propyl]-5,6-dimethyl-1,3-dihydro-1-oxo-isoindole 2-[N-methyl-N-(3-(pyridin-3-yl)-propyl)-3-amino-propyl]-5,6-dimethoxy-1,3-dihydro-1-oxo-isoindole 2-[N-methyl-N-((pyridin-3-yl)-methyl)-3-amino-propyl]-5,6-dimethoxy-1,3-dihydro-1-oxo-isoindole 2-[N-methyl-N-(2-(6,7-dimethoxy-isoquinolin-4-yl)-ethyl)-3-amino-propyl]-5,6-dimethoxy-1,3-dihydro-1-oxo-isoindole 2-[N-methyl-N-(2-(6,7-dimethoxy-isoquinolin-4-yl)-ethyl)-3-amino-propyl]-5,6-dimethyl-1,3-dihydro-1-oxo-isoindole 2-[N-methyl-N-((pyridin-3-yl)-methyl)-3-amino-propyl]-5,6-dimethyl-1,3-dihydro-1-oxo-isoindole 2-[N-methyl-N-((pyridin-3-yl)-methyl)-3-amino-propyl]-6,7-methylenedioxy-1-oxo-1,2,3,4-tetrahydro-isoquinoline 2-[N-methyl-N-((pyridine-3-yl)-methyl)-3-amino-propyl]-5,6-dimethyl-phthalimide 2-[N-methyl-N-(3-(pyridin-4-yl)-propyl)-3-amino-propyl]-5,6-dimethyl-phthalimide 2-[N-methyl-N-(2-(6,7-dimethoxy-isoquinolin-4-yl)ethyl)-3-aminopropyl]-5,6-dimethyl-phthalimide 2-[N-methyl-N-(2-(pyridin-2-yl)-ethyl)-3-amino-propyl]-5,6-dimethoxy-phthalimide 2-[N-methyl-N-(2-(6,7-dimethoxy-isoquinolin-4-yl)ethyl)-3-amino-propyl]-5,6-dimethoxy-phthalimide 2-[N-methyl-N-(2-(6,7-dimethoxy-isoquinolin-4-yl)ethyl)-3-amino-propyl]-6,7-methylenedioxy-1-oxo-1,2,3,4-tetrahydro-isoquinoline 2-[N-methyl-N-(2-(6,7-dimethoxy-isoquinolin-4-yl)ethyl)-3-amino-propyl]-6,7-methylenedioxy-1,2,3,4-tetrahydro-isoquinoline 2-[N-methyl-N-(3-(pyridin-4-yl)-propyl)-3-amino-propyl]-5,6-dimethoxy-1,3-dihydro-isoindole 2-[N-methyl-N-(2-(benzo[b]thien-3-yl)-ethyl)-3-amino-propyl]-6,7-dimethoxy-1-thioxo-1,2,3,4-tetrahydro-isoquinoline 2-[N-methyl-N-(2-(pyridin-2-yl)-ethyl)-3-amino-propyl]-6,7-dimethoxy-1-oxo-1,2,3,4-tetrahydro-isoquinoline 2-[N-methyl-N-(3-(pyridin-4-yl)-propyl)-3-amino-propyl]-6,7-dimethoxy-1-oxo-1,2,3,4-tetrahydro-isoquinoline 2-[N-methyl-N-(2-(pyridin-3-yl)-ethyl)-3-amino-propyl]-6,7-dimethoxy-1-1,2,3,4-tetrahydro-isoquinoline 2-[N-methyl-N-(2-(2-methyl-pyridin-6-yl)-ethyl)-3-amino-propyl]-6,7-dimethoxy-1-oxo-1,2,3,4-tetrahydro-isoquinoline 2-[N-methyl-N-(2-(pyridin-2-yl)-ethyl)-3-amino-propyl]-6,7-dimethoxy-1,2,3,4-tetrahydro-isoquinoline 2-[N-methyl-N-(3-(pyridin-3-yl)-propyl)-3-amino-propyl]-6,7-dimethoxy-1,2,3,4-tetrahydro-isoquinoline 2-[N-methyl-N-(3-(pyridin-4-yl)-propyl)-3-amino-propyl]-6,7-dimethoxy-1,2,3,4-tetrahydro-isoquinoline 2-[N-methyl-N-(2-(6,7-dimethoxy-isoquinolin-4-yl)ethyl)-3-amino-propyl]-b 6,7-dimethoxy-1,2,3,4-tetrahydro-isoquinoline 2-[N-methyl-N-(2-(pyridin-3-yl)-ethyl)-3-amino-propyl]-6,7-dimethoxy-1,2,3,4-tetrahydro-isoquinoline 2-[N-methyl-N-(2-(pyridin-2-yl)-ethyl)-3-amino-propyl]-6,7-dimethyl-1,-oxo-1,2,3,4-tetrahydro-isoquinoline 2-[N-methyl-N-(3-(pyridin-3-yl)-propyl)-3-amino-propyl]-6,7-dimethyl-1-oxo-1,2,3,4-tetrahydro-isoquinoline 2-[N-methyl-N-(3-(pyridin-4-yl)-propyl)-3-amino-propyl]-6,7-dimethyl-1-oxo-1,2,3,4-tetrahydro-isoquinoline 2-[N-methyl-N-(pyridin-3-yl-N-oxido)-propyl)-3-amino-propyl]-6,7-dimethyl-1-oxo-1,2,3,4-tetrahydro-isoquinoline 2-[N-methyl-N-((pyridin-3-yl)-methyl)-3-amino-propyl]-6,7-dimethyl-1-oxo-1,2,3,4-tetrahydro-isoquinoline 2-[N-methyl-N-(2-(6,7-dimethoxy-isoquinolin-4-yl)-ethyl)-3-amino-propyl]-6,7-dimethyl-1-oxo-1,2,3,4-tetrahydro-isoquinoline 2-[N-methyl-N-(2-(pyridin-3-yl)-ethyl)-3-amino-propyl]-6,7-dimethyl-1-oxo-1,2,3,4-tetrahydro-isoquinoline 2-[N-methyl-N-(2-(pyridin-2-yl)-ethyl)-3-amino-propyl]-6,7-dimethyl-1,2,3,4-tetrahydro-isoquinoline 2-[N-methyl-N-(3-(pyridin-3-yl)-propyl)-3-amino-propyl]-6,7-dimethyl-1,2,3,4-tetrahydro-isoquinoline 2-[N-methyl-N-(2-(pyridin-3-yl)-ethyl)-3-amino-propyl]-6,7-dimethyl-1,2,3,4-tetrahydro-isoquinoline 2-[N-methyl-N-(2-(pyridin-2-yl)-ethyl)-3-amino-propyl]-6,7-methylenedioxy-1-oxo-1,2,3,4-tetrahydro-isoquinoline 2-[N-methyl-N-(3-(pyridin-3-yl)-propyl)-3-amino-propyl]-6,7-methylenedioxy-1-oxo-1,2,3,4-tetrahydro-isoquinoline 2-[N-methyl-N-(3-(pyridin-3-yl-N-oxido)-propyl)-3-amino-propyl]-6,7-methylenedioxy-1-oxo-1,2,3,4-tetrahydro-isoquinoline 2-[N-methyl-N-(2-(pyridin-3-yl)-ethyl)-3-amino-propyl]-6,7-methylenedioxy-1-oxo-1,2,3,4-tetrahydro-isoquinoline 2-[N-methyl-N-(2-(2-methyl-pyridin-6-yl)-ethyl)-3-amino-propyl]-6,7-methylenedioxy-1-oxo-1,2,3,4-tetrahydro-isoquinoline 2-[N-methyl-N-(2-(pyridin-2-yl)-ethyl-3-amino-propyl]-6,7-methylenedioxy-1,2,3,4-tetrahydro-isoquinoline 2-[N-methyl-N-(3-(pyridin-3-yl)-propyl)-3-amino-propyl]-6,7-methylenedioxy-1,2,3,4-tetrahydro-isoquinoline 2-[N-methyl-N-(2-(pyridin-3-yl)-ethyl)-3-amino-propyl]-6,7-methylenedioxy-1,2,3,4-tetrahydro-isoquinoline 2-[N-methyl-N-(2-(pyridin-2-yl)-ethyl)-3-amino-propyl]-6,7-dimethoxy-1,3-dihydro-1-oxo-isoindole 2-[N-methyl-N-(3-(pyridin-4-yl)-propyl)-3-amino-propyl]-5,6-dimethoxy-1,3-dihydro-1-oxo-isoindole 2-[N-methyl-N-(3-(pyridin-3-yl-N-oxido)-propyl)-3-amino-propyl]-5,6-dimethoxy-1,3-dihydro-1-oxo-isoindole 2-[N-methyl-N-(2-(pyridin-3-yl)-ethyl)-3-amino-propyl]-5,6-dimethoxy-1,3-dihydro-1-oxo-isoindole 2-[N-methyl-N-(2-(2-methyl-pyridin-6-yl)-ethyl)-3-amino-propyl]-5,6-dimethoxy-1,3-dihydro-1-oxo-isoindole 2-[N-methyl-N-(2-(6,7-dimethoxy-isoquinolin-4-yl)-ethyl)-3-amino-propyl]-5,6-dimethyl-1,3-dihydro-isoindole 2-[N-methyl-N-(2-(pyridin-3-yl)-ethyl(-3-amino-propyl]-5,6-dimethoxy-1,3-1,3-dihydro-isoindole 2-[N-methyl-N-(2-(pyridin-2-yl)-ethyl)-3-amino-propyl]-5,6-dimethyl-1,3-dihydro-1-oxo-isoindole 2-[N-methyl-N-(3-pyridin-3-yl)-propyl)-3-amino-propyl]-5,6-dimethyl-1,3-dihydro-1-oxo-isoindole 2-[N-methyl-N-(2-(pyridin-3-yl)-ethyl)-3-amino-propyl]-5,6-dimethyl-1,3-dihydro-1-oxo-isoindole 2-[N-methyl-N-(2-(2-methyl-pyridin-6-yl)-ethyl)-3-amino-propyl]-5,6-dimethyl-1,3-dihydro-1-oxo-isoindole 2-[N-methyl-N-(3-(pyridin-3-yl)-propyl)-3-amino-propyl]-5,6-dimethyl-1,3-dihydro-isoindole 2-[N-methyl-N-(2-(pyridin-3-yl)-ethyl)-3-amino-propyl]-5,6-dimethyl-1,3-dihydro-isoindole 2-[N-methyl-N-(2-(pyridin-2-yl)-ethyl)-3-amino-propyl]-5,6-methylenedioxy-1,3-dihydro-1-oxo-isoindole 2-[N-methyl-N-(3-(pyridin-3-yl)-propyl)-3-amino-propyl]-5,6-methylenedioxy-1,3-dihydro-1-oxo-isoindole 2-[N-methyl-N-(3-(pyridin-4-yl)-propyl)-3-amino-propyl]-5,6-methylenedioxy-1,3-dihydro-1-oxo-isoindole 2-[N-methyl-N-(3-(pyridin-3-yl-N-oxido)-propyl)-3-amino-propyl]-5,6-methylenedioxy-1,3-dihydro-1-oxo-isoindole 2-[N-methyl-N-(2-(6,7-dimethoxy-isoquinolin-4-yl)-ethyl)-3-aminopropyl]-5,6-methylenedioxy-1,3-dihydro-1-oxo-isoindole 2-[N-methyl-N-(2-(pyridin-3-yl)-ethyl)-3-amino-propyl]-5,6-methylenedioxy-1,3-dihydro-1-oxo-isoindole 2-[N-methyl-N-(2-(pyridin-2-yl)-ethyl)-3-amino-propyl]-5,6-methylenedioxy-1,3-dihydro-isoindole 2-[N-methyl-N-(2-(2-methyl-pyridin-6-yl)-ethyl)-3-amino-propyl]-5,6-methylenedioxy-1,3-dihydro-isoindole 2-[N-methyl-N-(2-(benzo[b]thien-2-yl)-ethyl)-3-amino-propyl]-5,6-dimethoxy-1,3-dihydro-1-oxo-isoindole 2-[N-methyl-N-(2-(4-methoxy-benzo[b]thien-3-yl)-ethyl)-3-amino-propyl]-5,6-dimethoxy-1,3-dihydro-1-oxo-isoindole 2-[N-methyl-N-(2-(5-methoxy-benzo[b]thien-3-yl)-ethyl)-3-amino-propyl]-5,6-dimethoxy-1,3-dihydro-1-oxo-isoindole 2-[N-methyl-N-(2-(6-methoxy-benzo[b]thien-3-yl)-ethyl)-3-amino-propyl]-5,6-dimethoxy-1,3-dihydro-1-oxo-isoindole 2-[N-methyl-N-(2-(5-methyl-benzo[b]thien-3-yl)-ethyl)-3-amino-propyl]-5,6-dimethoxy-1,3-dihydro-1-oxo-isoindole 2-[N-methyl-N-(2-(5-bromo-benzo[b]thien-3-yl)-ethyl)-3-amino-propyl]-5,6-dimethoxy-1,3-dihydro-1-oxo-isoindole 2-[N-methyl-N-(2-(6-methylsulphonyloxy-benzo[b]thien-3-yl)-ethyl)-3-amino-propyl]-5,6-dimethoxy-1,3-dihydro-1-oxo-isoindole 2-[N-methyl-N-(2-(6-carboxymethoxy-benzo[b]thien-3-yl)-ethyl)-3-amino-propyl]-5,6-dimethoxy-1,3-dihydro-1-oxo-isoindole 2-[N-methyl-N-(2-(5-methyl-thien-2-yl)-ethyl)-3-amino-propyl]-5,6-dimethoxy-1,3-dihydro-1-oxo-isoindole 2-[N-methyl-N-(2-(5-bromo-thien-2-yl)-ethyl)-3-amino-propyl]-5,6-dimethoxy-1,3-dihydro-1-oxo-isoindole 2-[N-methyl-N-(2-(2,5-dimethyl-thien-3-yl)-ethyl)-3-amino-propyl]-5,6-dimethoxy-1,3-dihydro-1-oxo-isoindole 2-[N-methyl-N-(2-(5-methoxy-indol-3-yl)-ethyl)-3-amino-propyl]-5,6-dimethoxy-1,3-dihydro-1-oxo-isoindole 2-[N-methyl-N-(2-(5-benzyloxy-indol-3-yl)-ethyl)-3-amino-propyl]-5,6-dimethoxy-1,3-dihydro-1-oxo-isoindole 2-[N-methyl-N-(2-(5-bromo-indol-3-yl)-ethyl)-3-amino-propyl]-5,6-dimethoxy-1,3-dihydro-1-oxo-isoindole 2-[N-methyl-N-(2-(5-methyl-indol-3-yl)-ethyl)-3-amino-propyl]-5,6-dimethoxy-1,3-dihydro-1-oxo-isoindole 2-[N-methyl-N-(2-(7-methyl-indol-3-yl)-ethyl)-3-amino-propyl]-5,6-dimethoxy-1,3-dihydro-1-oxo-isoindole 2-[N-methyl-N-(2-(benzo[b]furan-2-yl)-ethyl)-3-amino-propyl]-5,6-dimethoxy-1,3-dihydro-1-oxo-isoindole 2-[N-methyl-N-(2-(benzo[b]furan-3-yl)-ethyl)-3-amino-propyl]-5,6-dimethoxy-1,3-dihydro-1-oxo-isoindole 2-[N-methyl-N-(2-(6-methoxy-benzo[b]furan-3-yl)-ethyl)-3-aminopropyl]-5,6-dimethoxy-1,3-dihydro-1-oxo-isoindole 2-[N-methyl-N-(2-(7-methoxy-benzo[b]furan-3-yl)-ethyl)-3-amino-propyl]-5,6-dimethoxy-1,3-dihydro-1-oxo-isoindole 2-[N-methyl-N-(2-(furan-2-yl)-ethyl)-3-amino-propyl]-5,6-dimethoxy-1,3-dihydro-1-oxo-isoindole 2-[N-methyl-N-(2-(furan-3-yl)-ethyl)-3-amino-propyl]-5,6-dimethoxy-1,3-dihydro-1-oxo-isoindole 2-[N-methyl-N-(2-(5-methyl-furan-2-yl)-ethyl)-3-amino-propyl]-5,6-dimethoxy-1,3-dihydro-1-oxo-isoindole 2-[N-methyl-N-(2-(2,5-dimethyl-furan-3-yl)-ethyl)-3-amino-propyl]-5,6-dimethoxy-1,3-dihydro-1-oxo-isoindole 2-[N-methyl-N-(2-(imidazol-4(5)-yl)-ethyl)-3-amino-propyl]-5,6-dimethoxy-1,3-dihydro-1-oxo-isoindole 2-[N-methyl-N-(2-(1-methyl-imidazol-4-yl)-ethyl)-3-amino-propyl]-5,6-dimethoxy-1,3-dihydro-1-oxo-isoindole 2-[N-methyl-N-(2-(imidazol-1-yl)-ethyl)-3-amino-propyl]-5,6-dimethoxy-1,3-dihydro-1-oxo-isoindole 2-[N-methyl-N-(2-(1H-benzo[d]imidazol-1-yl)-ethyl)-3-amino-propyl]-5,6-dimethoxy-1,3-dihydro-1-oxo-isoindole 2-[N-methyl-N-(2-(4-methyl-thiazol-5-yl)-ethyl)-3-amino-propyl]-5,6-dimethoxy-1,3-dihydro-1-oxo-isoindole 2-[N-methyl-N-(2-(1-methyl-pyrrol-2-yl)-ethyl)-3-amino-propyl]-5,6-dimethoxy-1,3-dihydro-1-oxo-isoindole 2-[N-methyl-N-(2-(benzo[b]thien-2-yl)-ethyl)-3-amino-propyl]-5,6-methylenedioxy-1,3-dihydro-1-oxo-isoindole 2-[N-methyl-N-(2-(4-methoxy-benzo[b]thien-3-yl)-ethyl)-3-amino-propyl]-5,6-methylenedioxy-1,3-dihydro-1-oxo-isoindole 2-[N-methyl-N-(2-(5-methoxy-benzo[b]thien-3-yl)-ethyl)-3-amino-propyl]-5,6-methylenedioxy-1,3-dihydro-1-oxo-isoindole 2-[N-methyl-N-(2-(6-methoxy-benzo[b]thien-3-yl)-ethyl)-3-amino-propyl]-5,6-methylenedioxy-1,3-dihydro-1-oxo-isoindole 2-[N-methyl-N-(2-(5-methyl-benzo[b]thien-3-yl)-ethyl)-3-amino-propyl]-5,6-methylenedioxy-1,3-dihydro-1-oxo-isoindole 2-[N-methyl-N-(2-(5-bromo-benzo[b]thien-3-yl)-ethyl)-3-amino-propyl]-5,6-methylenedioxy-1,3-dihydro-1-oxo-isoindole 2-[N-methyl-N-(2-(6-methylsulphonyloxy-benzo[b]thien-3-yl)-ethyl)-3-amino-propyl]-5,6-methylenedioxy-1,3-dihydro-1-oxo-isoindole 2-[N-methyl-N-(2-(6-carboxymethoxy-benzo[b]thien-3-yl)-ethyl)-3-amino-propyl]-5,6-methylenedioxy-1,3-dihydro-1-oxo-isoindole 2-[N-methyl-N-(2-(5-methyl-thien-2-yl)-ethyl)-3-amino-propyl]-5,6-methylenedioxy-1,3-dihydro-1-oxo-isoindole 2-[N-methyl-N-(2-(5-bromo-thien-2-yl)-ethyl)-3-amino-propyl]-5,6-methylenedioxy-1,3-dihydro-1-oxo-isoindole 2-[N-methyl-N-(2-(2,5-dimethyl-thien-3-yl)-ethyl)-3-amino-propyl]-5,6-methylenedioxy-1,3-dihydro-1-oxo-isoindole 2-[N-methyl-N-(2-(5-methoxy-indol-3-yl)-ethyl)-3-amino-propyl]-5,6-methylenedioxy-1,3-dihydro-1-oxo-isoindole 2-[N-methyl-N-(2-(5-benzyloxy-indol-3-yl)-ethyl)-3-amino-propyl]-5,6-methylenedioxy-1,3-dihydro-1-oxo-isoindole 2-[N-methyl-N-(2-(5-bromo-indol-3-yl)-ethyl)-3-amino-propyl]-5,6-methylenedioxy-1,3-dihydro-1-oxo-isoindole 2-[N-methyl-N-(2-(5-methyl-indol-3-yl)-ethyl)-3-amino-propyl]-5,6-methylenedioxy-1,3-dihydro-1-oxo-isoindole 2-[N-methyl-N-(2-(7-methyl-indol-3-yl)-ethyl)-3-amino-propyl]-5,6-methylenedioxy-1,3-dihydro-1-oxo-isoindole 2-[N-methyl-N-(2-(benzo[b]furan-2-yl)-ethyl)-3-amino-propyl]-5,6-methylenedioxy-1,3-dihydro-1-oxo-isoindole 2-[N-methyl-N-(2-(benzo[b]furan-3-yl)-ethyl)-3-amino-propyl]-5,6-methylenedioxy-1,3-dihydro-1-oxo-isoindole 2-[N-methyl-N-(2-(6-methoxy-benzo[b]furan-3-yl)-ethyl)-3-amino-propyl]-5,6-methylenedioxy-1,3-dihydro-1-oxo-isoindole 2-[N-methyl-N-(2-(7-methoxy-benzo[b]furan-3-yl)-ethyl)-3A-amino-propyl]-5,6-methylenedioxy-1,3-dihydro-1-oxo-isoindole 2-[N-methyl-N-(2-(furan-2-ethyl)-3-amino-propyl]-5,6-methylenedioxy-1,3-dihydro-1-oxo-isoindole 2-[N-methyl-N-(2-furan-3-yl)-ethyl)-3-amino-propyl]-5,6-methylenedioxy-1,3-dihydro-1-oxo-isoindole 2-[N-methyl-N-(2-(5-methyl-furan-2-yl)-ethyl)-3-amino-propyl]-5,6-methylenedioxy-1,3-dihydro-1-oxo-isoindole 2-[N-methyl-N-(2-(2,5-dimethyl-furan-3-yl)-ethyl)-3-amino-propyl]-5,6 -methylenedioxy-1,3-dihydro-1-oxo-isoindole 2-[N-methyl-N-(2-(imidazolyl-4(5)-ethyl)-3-amino-propyl]-5,6-methylenedioxy-1,3-dihydro-1-oxo-isoindole 2-[N-methyl-N-(2-(1-methyl-imidazol-4-yl)-ethyl)-3-amino-propyl]-5,6-methylenedioxy-1,3-dihydro-1-oxo-isoindole 2-[N-methyl-N-(2-(imidazol-1-yl)-ethyl)-3-amino-propyl]-5,6-methylenedioxy-1,3-dihydro-1-oxo-isoindole 2-[N-methyl-N-(2-(1H-benzo[d]imidazol-1-yl)-ethyl)-3-amino-propyl]-5,6-methylenedioxy-1,3-dihydro-1-oxo-isoindole 2-[N-methyl-N-(2-(4-methyl-thiazol-5-yl)-ethyl)-3-amino-propyl]-4,5-methylenedioxy-1,3-dihydro-1-oxo-isoindole 2-[N-methyl-N-(2-(1-methyl-pyrrol-2-yl)-ethyl)-3-amino-propyl]-5,6-methylenedioxy-1,3-dihydro-1-oxo-isoindole 2-[N-methyl-N-(2-(thien-2-yl)-ethyl)-3-amino-propyl]-5,6-methylenedioxy-1,3-dihydro-1-oxo-isoindole 2-[N-methyl-N-(thien-3-yl)-ethyl)-3-amino-propyl]-5,6-methylenedioxy-1,3-dihydro-1-oxo-isoindole 2-[N-methyl-N-(2-(benzo[b]thien-3-yl)-ethyl)-3-amino-propyl]-5,6-methylenedioxy-1,3-dihydro-1-oxo-isoindole 2-[N-methyl-N-(2-(indol-3-yl)-ethyl)-3-amino-propyl]-5,6-methylenedioxy-1,3-dihydro-1-oxo-isoindole 2-[N-methyl-N-(2-(benzo[b]thien-2-yl)-ethyl)-3-amino-propyl]-5,6-dimethyl-1,3-dihydro-1-oxo-isoindole 2-[N-methyl-N-(2-(4-methoxy-benzo[b]thien-3-yl)-ethyl)-3-amino-propyl]-5,6-dimethyl-1,3-dihydro-1-oxo-isoindole 2-[N-methyl-N-(2-(5-methoxy-benzo[b]thien-3-yl)-ethyl)-3-amino-propyl]-5,6-dimethyl-1,3-dihydro-1-oxo-isoindole 2-[N-methyl-N-(2-(6-methoxy-benzo[b]thien-3-yl)-ethyl)-3-amino-propyl]-5,6-dimethyl-1,3-dihydro-1-oxo-isoindole 2-[N-methyl-N-(2-(5-methyl-benzo[b]thien-3-yl)-ethyl)-3-amino-propyl]-5,6-dimethyl-1,3-dihydro-1-oxo-isoindole 2-[N-methyl-N-(2-(5-bromo-benzo[b]thien-3-yl)-ethyl)-3-amino-propyl]-5,6-dimethyl-1,3-dihydro-1-oxo-isoindole 2-[N-methyl-N-(2-(6-methylsulphonyloxy-benzo[b]thien-3-yl)-ethyl)-3-amino-propyl]-5,6-dimethyl-1,3-dihydro-1-oxo-isoindole 2-[N-methyl-N-(2-(6-carboxymethoxy-benzo[b]thien-3-yl)-ethyl)-3-amino-propyl]-5,6-dimethyl-1,3-dihydro-1-oxo-isoindole 2-[N-methyl-N-(2-(5-methyl-thien-2-yl)-ethyl)-3-amino-propyl]-5,6-dimethyl-1,3-dihydro-1-oxo-isoindole 2-[N-methyl-N-(2-(5-bromo-thien-2-yl)-ethyl)-3-amino-propyl]-5,6-dimethyl-1,3-dihydro-1-oxo-isoindole 2-[N-methyl-N-(2-(2,5-dimethyl-thien-3-yl)-ethyl)-3-amino-propyl]-5,6-dimethyl-1,3-dihydro-1-oxo-isoindole 2-[N-methyl-N-(2-(5-methoxy-indol-3-yl)-ethyl)-3-amino-propyl]-5,6-dimethyl-1,3-dihydro-1-oxo-isoindole 2-[N-methyl-N-(2-(5-benzyloxy-indol-3-yl)-ethyl)-3-amino-propyl]-5,6-dimethyl-1,3-dihydro-1-oxo-isoindole 2-[N-methyl-N-(2-(5-bromo-indol-3-yl)-ethyl)-3-amino-propyl]-5,6-dimethyl-1,3-dihydro-1-oxo-isoindole 2-[N-methyl-N-(2-(5-methyl-indol-3-yl)-ethyl)-3-amino-propyl]-5,6-dimethyl-1,3-dihydro-1-oxo-isoindole 2-[N-methyl-N-(2-(7-methyl-indol-3-yl)-ethyl)-3-amino-propyl]-5,6-dimethyl-1,3-dihydro-1-oxo-isoindole 2-[N-methyl-N-(2-(benzo[b]furan-2-yl)-ethyl)-3-amino-propyl]-5,6-dimethyl-1,3-dihydro-1-oxo-isoindole 2-[N-methyl-N-(2-(benzo[b]furan-3yl)-ethyl)-3-amino-propyl]-5,6-dimethyl-1,3-dihydro-1-oxo-isoindole 2-[N-methyl-N-(2-(6-methoxy-benzo[b]furan-3-yl)-ethyl)-3-amino-propyl]-5,6-dimethyl-1,3-dihydro-1-oxo-isoindole 2-[N-methyl-N-(2-(7-methoxy-benzo[b]furan-3-yl)-ethyl)-3-amino-propyl]-5,6-dimethyl-1,3-dihydro-1-oxo-isoindole 2-[N-methyl-N-(2-(furan-2-yl)-ethyl)-3-amino-propyl]-5,6-dimethyl-1,3-dihydro-1-oxo-isoindole 2-[N-methyl-N-(2-(furan-3-yl)-ethyl)-3-amino-propyl]-5,6-dimethyl-1,3-dihydro-1-oxo-isoindole 2-[N-methyl-N-(2-(5-methyl-furan-2-yl)-ethyl)-3-amino-propyl]-5,6-dimethyl-1,3-dihydro-1-oxo-isoindole 2-[N-methyl-N-(2-(2,5-dimethyl-furan-3-yl)-ethyl)-3-amino-propyl]-5,6-dimethyl-1,3-dihydro-1-oxo-isoindole 2-[N-methyl-N-(2-(imidazol-4(5)-yl)-ethyl)-3-amino-propyl]-5,6-dimethyl-1,3-dihydro-1-oxo-isoindole 2-[N-methyl-N-(2-(1-methyl-imidazol-4-yl)-ethyl)-3-amino-propyl]-5,6-dimethyl-1,3-dihydro-1-oxo-isoindole 2-[N-methyl-N-(2-(imidazol-1-yl)-ethyl)-3-amino-propyl]-5,6-dimethyl-1,3-dihydro-1-oxo-isoindole 2-[N-methyl-N-(2-(1H-benzo[d]imidazol-1-yl)-ethyl)-3-amino-propyl]-5,6-dimethyl-1,3-dihydro-1-oxo-isoindole 2-[N-methyl-N-(2-(4-methyl-thiazol-5-yl)-ethyl)-3-amino-propyl]-5,6-dimethyl-1,3-dihydro-1-oxo-isoindole 2-[N-methyl-N-(2-(1-methyl-pyrrol-2-yl)-ethyl)-3-amino-propyl]-5,6-dimethyl-1,3-dihydro-1-oxo-isoindole 2-[N-methyl-N-(2-(thien-2-yl)-ethyl)-3-amino-propyl]-5,6-dimethyl-1,3-dihydro-1-oxo-isoindole 2-[N-methyl-N-(2-(thien-3-yl)-ethyl)-3-amino-propyl]-5,6-dimethyl-1,3-dihydro-1-oxo-isoindole 2-[N-methyl-N-(2-(benzo[b]thien-3-yl)-ethyl)-3-amino-propyl]-5,6-dimethyl-1,3-dihydro-1-oxo-isoindole 2-[N-methyl-N-(2-(indol-3-yl)-ethyl)-3-amino-propyl]-5,6-dimethyl-1,3-dihydro-1-oxo-isoindole 2-[N-methyl-N-(2-(benzo[b]thien-2-yl)-ethyl)-3-amino-propyl]-5,6-dimethoxy-1-oxo-1,2,3,4-tetrahydro-isoquinoline 2-[N-methyl-N-(2-(4-methoxy-benzo[b]thien-3-yl)-ethyl)-3-amino-propyl]-5,6-dimethoxy-1-oxo-1,2,3,4-tetrahydro-isoquinoline 2-[N-methyl-N-(2-(5-methoxy-benzo[b]thien-3-yl)-ethyl)-3-amino-propyl]-5,6-dimethoxy-1-oxo-1,2,3,4-tetrahydro-isoquinoline 2-[N-methyl-N-(2-(6-methoxy-benzo[b]thien-3-yl)-ethyl)-3-amino-propyl]-5,6-dimethoxy-1-oxo-1,2,3,4-tetrahydro-isoquinoline 2-[N-methyl-N-(2-(5-methyl-benzo[b]thien-3-yl)-ethyl)-3-amino-propyl]-5,6-dimethoxy-1-oxo-1,2,3,4-tetrahydro-isoquinoline 2-[N-methyl-N-(2-(5-bromo-benzo[b]thien-3-yl)-ethyl)-3-amino-propyl]-5,6-dimethoxy-1-oxo-1,2,3,4-tetrahydro-isoquinoline 2-[N-methyl-N-(2-(6-methylsulphonyloxy-benzo[b]thien-3-yl)-3-amino-propyl]-5,6-dimethoxy-1-oxo-1,2,3,4-tetrahydro-isoquinoline 2-[N-methyl-N-(2-(6-carboxymethoxy-benzo[b]thien-3-yl)-ethyl)-3-amino-propyl]-5,6-dimethoxy-1-oxo-1,2,3,4-tetrahydro-isoquinoline 2-[N-methyl-N-(2-(5-methyl-thien-2-yl)-ethyl)-3-amino-propyl]-5,6-dimethoxy-1-oxo-1,2,3,4-tetrahydro-isoquinoline 2-[N-methyl-N-(2-(5-bromo-thien-2-yl)-ethyl)-3-amino-propyl]-5,6-dimethoxy-1-1,2,3,4-tetrahydro-isoquinoline 2-[N-methyl-N-(2-(2,5-dimethyl-thien-3-yl)-ethyl)-3-amino-propyl]-5,6-dimethoxy-1-oxo-1,2,3,4-tetrahydro-isoquinoline 2-[N-methyl-N-(2-(5-methoxy-indol-3-yl)-ethyl)-3-amino-propyl]-5,6-dimethoxy-1-oxo-1,2,3,4-tetrahydro-isoquinoline 2-[N-methyl-N-(2-(5-benzyloxy-indol-3-yl)-ethyl-3-amino-propyl]-5,6-dimethoxy-1-oxo-1,2,3,4-tetrahydro-isoquinoline 2-[N-methyl-N-(2-(5-bromo-indol-3-yl)-ethyl)-3-amino-propyl]-5,6-dimethoxy-1-oxo-1,2,3,4-tetrahydro-isoquinoline 2-[N-methyl-N-(2-(5-methyl-indol-3-yl)-ethyl)-3-amino-propyl]-5,6-dimethoxy-1-oxo-1,2,3,4-tetrahydro-isoquinoline 2-[N-methyl-N-(2-(7-methyl-indol-3-yl)-ethyl)-3-amino-propyl]-5,6-dimethoxy-1-oxo-1,2,3,4-tetrahydro-isoquinoline 2-[N-methyl-N-(2-(benzo[b]furan-3-yl)-ethyl)-3-amino-propyl]-5,6-dimethoxy-1-oxo-1,2,3,4-tetrahydro-isoquinoline 2-[N-methyl-N-(2-(6-methoxy-benzo[b]furan-3-yl)-ethyl)-3-amino-propyl]-5,6-dimethoxy-1-oxo-1,2,3,4-tetrahydro-isoquinoline 2-[N-methyl-N-(2-(7-methoxy-benzo[b]furan-3-yl)-ethyl)-3-amino-propyl]-5,6-dimethoxy-1-oxo-1,2,3,4-tetrahydro-isoquinoline 2-[N-methyl-N-(2-(furan-2-yl)-ethyl)-3-amino-propyl]-5,6-dimethoxy-1-oxo-1,2,3,4-tetrahydro-isoquinoline 2-[N-methyl-N-(2-(furan-3-yl)-ethyl)-3-amino-propyl]-5,6-dimethoxy-1-oxo-1,2,3,4-tetrahydro-isoquinoline 2-[N-methyl-N-(2-(5-methyl-furan-2-yl)-ethyl)-3-amino-propyl]-5,6-dimethoxy-1-oxo-1,2,3,4-tetrahydro-isoquinoline 2-[N-methyl-N-(2-(2,5-dimethyl-furan-3-yl)-ethyl)-3-amino-propyl]-5,6-dimethoxy-1-oxo-1,2,3,4-tetrahydro-isoquinoline 2-[N-methyl-N-(2-(imidazol-4(5)-yl)-ethyl)-3-amino-propyl]-5,6-dimethoxy-1-oxo-1,2,3,4-tetrahydro-isoquinoline 2-[N-methyl-N-(2-(1-methyl-imidazol-4-yl)-ethyl)-3-amino-propyl]-5,6-dimethoxy-1-oxo-1,2,3,4-tetrahydro-isoquinoline 2-[N-methyl-N-(2-(imidazol-1-yl)-ethyl)-3-amino-propyl]-5,6-dimethoxy-1-oxo-1,2,3,4-tetrahydro-isoquinoline 2-[N-methyl-N-(2-(1H-benzo[d]imidazol-1-yl)-ethyl)-3-amino-propyl]-5,6-dimethoxy-1-oxo-1,2,3,4-tetrahydro-isoquinoline 2-[N-methyl-N-(2-(4-methyl-thiazol-5-yl)-ethyl)-3-amino-propyl]-5,6-dimethoxy-1-oxo-1,2,3,4-tetrahydro-isoquinoline 2-[N-methyl-N-(2-(1-methyl-pyrrol-2-yl)-ethyl)-3-amino-propyl]-5,6-dimethoxy-1-oxo-1,2,3,4-tetrahydro-isoquinoline 2-[N-methyl-N-(2-(thien-2-yl)-ethyl)-3-amino-propyl]-5,6-methylenedioxy-1-oxo-1,2,3,4-tetrahydro-isoquinoline 2-[N-methyl-N-(2-(thien-3-yl)-ethyl)-3-amino-propyl]-5,6-methylenedioxy-1-oxo-1,2,3,4-tetrahydro-isoquinoline 2-[N-methyl-N-(2-(benzo[b]thien-3-yl)-ethyl)-3-amino-propyl]-5,6-methylenedioxy-1-oxo-1,2,3,4-tetrahydro-isoquinoline 2-[N-methyl-N-(2-(indol-3-yl)-ethyl)-3-amino-propyl]-5,6-methylenedioxy-1-oxo-1,2,3,4-tetrahydro-isoquinoline 2-[N-methyl-N-(2-(benzo[b]furan-2-yl)-ethyl)-3-amino-propyl]-5,6-methylenedioxy-1-oxo-1,2,3,4-tetrahydro-isoquinoline 2-[N-methyl-N-(2-(benzo[b]thien-2-yl)-ethyl)-3-amino-propyl]-5,6-dimethyl-1-oxo-1,2,3,4-tetrahydro-isoquinoline 2-[N-methyl-N-(2-(4-methoxy-benzo[b]thien-3-yl)-ethyl)-3-amino-propyl]-5,6-dimethyl-1-oxo-1,2,3,4-tetrahydro-isoquinoline 2-[N-methyl-N-(2-(5-methoxy-benzo[b]thien-3-yl)-ethyl)-3-amino-propyl]-5,6-dimethyl-1-oxo-1,2,3,4-tetrahydro-isoquinoline 2-[N-methyl-N-(2-(6-methoxy-benzo[b]thien-3-yl)-ethyl)-3-amino-propyl]-5,6-dimethyl-1-oxo-1,2,3,4-tetrahydro-isoquinoline 2-[N-methyl-N-(2-(5-methyl-benzo[b]thien-3-yl)-ethyl)-3-amino-propyl]-5,6-dimethyl-1-oxo-1,2,3,4-tetrahydro-isoquinoline 2-[N-methyl-N-(2-(5-bromo-benzo[b]thien-3-yl)-ethyl)-3-amino-propyl]-5,6-dimethyl-1-oxo-1,2,3,4-tetrahydro-isoquinoline 2-[N-methyl-N-(2-(6-methylsulphonyloxy-benzo[b]thien-3-yl)-ethyl)-3-amino-propyl]-5,6-dimethyl-1-oxo-1,2,3,4-tetrahydro-isoquinoline 2-[N-methyl-N-(2-(6-carboxymethoxy-benzo[b]thien-3-yl)-ethyl)-3-amino-propyl]-5,6-dimethyl-1-oxo-1,2,3,4-tetrahydro-isoquinoline 2-[N-methyl-N-(2-(5-methyl-thien-2-yl)-ethyl)-3-amino-propyl]-5,6-dimethyl-1-oxo-1,2,3,4-tetrahydro-isoquinoline 2-[N-methyl-N-(2-(5-bromo-thien-2-yl)-ethyl)-3-amino-propyl]-5,6-dimethyl-1-oxo-1,2,3,4-tetrahydro-isoquinoline 2-[N-methyl-N-(2-(2,5-dimethyl-thien-3-yl)-ethyl)-3-amino-propyl]-5,6-dimethyl-1-oxo-1,2,3,4-tetrahydro-isoquinoline 2-[N-methyl-N-(2-(5-methoxy-indol-3-yl)-ethyl)-3-amino-propyl]-5,6-dimethyl-1-dimethyl-1-oxo-1,2,3,4-tetrahydro-isoquinoline 2-[N-methyl-N-(2-(5-benzyloxy-indol-3-yl)-ethyl)-3-amino-propyl]-5,6-dimethyl-1-oxo-1,2,3,4-tetrahydro-isoquinoline 2-[N-methyl-N-(2-(5-bromo-indol-3-yl)-ethyl)-3-amino-propyl]-5,6-dimethyl-1-oxo-1,2,3,4-tetrahydro-isoquinoline 2-[N-methyl-N-(2-(5-methyl-indol-3-yl)-ethyl)-3-amino-propyl]-5,6-dimethyl-1-oxo-1,2,3,4-tetrahydro-isoquinoline 2-[N-methyl-N-(2-(7-methyl-indol-3-yl)-ethyl)-3-amino-propyl]-5,6-dimethyl-1-oxo-1,2,3,4-tetrahydro-isoquinoline 2-[N-methyl-N-(2-(benzo[b]furan-3-yl)-ethyl)-3-amino-propyl]-5,6-dimethyl-1-oxo-1,2,3,4-tetrahydro-isoquinoline 2-[N-methyl-N-(2-(6-methoxy-benzo[b]furan-3-yl)-ethyl)-3-amino-propyl]-5,6-dimethyl-1-oxo-1,2,3,4-tetrahydro-isoquinoline 2-[N-methyl-N-(2-(7-methoxy-benzo[b]furan-3-yl)-ethyl)-3-amino-propyl]-5,6-dimethyl-1-oxo-1,2,3,4-tetrahydro-isoquinoline 2-[N-methyl-N-(2-(furan-2-yl)-ethyl)-3-amino-propyl]-5,6-dimethyl-1-oxo-1,2,3,4-tetrahydro-isoquinoline 2-[N-methyl-N-(2-(furan-3-yl)-ethyl)-3-amino-propyl]-5,6-dimethyl-1-oxo-1,2,3,4-tetrahydro-isoquinoline
2-[N-methyl-N-(2-(5-methyl-furan-2-yl)-ethyl)-3-amino-propyl]-5,6-dimethyl-1-oxo-1,2,3,4-tetrahydro-isoquinoline
2-[N-methyl-N-(2-(2,5-dimethyl-furan-3-yl)-ethyl)-3-amino-propyl]-5,6-dimethyl-1-oxo-1,2,3,4-tetrahydro-isoquinoline
2-[N-methyl-N-(2-(imidazol-4(5)-yl)-ethyl)-3-amino-propyl]-5,6-dimethyl-1-oxo-1,2,3,4-tetrahydro-isoquinoline
2-[N-methyl-N-(2-(1-methyl-imidazol-4-yl)-ethyl)-3-amino-propyl]-5,6-dimethyl-1-oxo-1,2,3,4-tetrahydro-isoquinoline
2-[N-methyl-N-(2-(imidazol-1-yl)-ethyl)-3-amino-propyl]-5,6-dimethyl-1-oxo-1,2,3,4-tetrahydro-isoquinoline
2-[N-methyl-N-(2-(1H-benzo[d]imidazol-1-yl)-ethyl)-3-amino-propyl]-5,6-dimethyl-1-oxo-1,2,3,4-tetrahydro-isoquinoline
2-[N-methyl-N-(2-(4-methyl-thiazol-4-yl)-ethyl)-3-amino-propyl]-5,6-dimethyl-1-oxo-1,2,3,4-tetrahydro-isoquinoline
2-[N-methyl-N-(2-(1-methyl-pyrrol-2-yl)-ethyl)-3-amino-propyl]-5,6-dimethyl-1-oxo-1,2,3,4-tetrahydro-isoquinoline
2-[N-methyl-N-(2-(thien-2-yl)-ethyl)-3-amino-propyl]-5,6-dimethyl-1-oxo-1,2,3,4-tetrahydro-isoquinoline
2-[N-methyl-N-(2-(thien-3-yl)-ethyl)-3-amino-propyl]-5,6-dimethyl-1-oxo-1,2,3,4-tetrahydro-isoquinoline
2-[N-methyl-N-(2-(benzo[b]thien-3-yl)-ethyl)-3-amino-propyl]-5,6-dimethyl-1-oxo-1,2,3,4-tetrahydro-isoquinoline
2-[N-methyl-N-(2-(indol-3-yl)-ethyl)-3-amino-propyl]-5,6-dimethyl-1-oxo-1,2,3,4-tetrahydro-isoquinoline
2-[N-methyl-N-(2-(benzo[b]furan-2-yl)-ethyl)-3-amino-propyl]-5,6-dimethyl-1-oxo-1,2,3,4-tetrahydro-isoquinoline
2-[N-methyl-N-(3-(thien-2-yl)-propyl)-3-amino-propyl]-5,6-dimethoxy-1,3-dihydro-1-oxo-isoindole
2-[N-methyl-N-(4-(thien-2-yl)-butyl)-3-amino-propyl]-5,6-dimethoxy-1,3-dihydro-1-oxo-isoindole
2-[N-methyl-N-(5-(thien-2-yl)-pentyl)-3-amino-propyl]-5,6-dimethoxy-1,3-dihydro-1-oxo-isoindole
2-[N-methyl-N-(3-(thien-3-yl)-propyl)-3-amino-propyl]-5,6-dimethoxy-1,3-dihydro-1-oxo-isoindole
2-[N-methyl-N-(4-(thien-3-yl)-butyl)-3-amino-propyl]-5,6-dimethoxy-1,3-dihydro-1-oxo-isoindole
2-[N-methyl-N-(5-(thien-3-yl)-pentyl)-3-amino-propyl]-5,6-dimethoxy-1,3-oxo-isoindole
2-[N-methyl-N-(3-(benzo[b]thien-3-yl)-propyl)-3-amino-propyl]-5,6-dimethoxy-1,3-dihydro-1-oxo-isoindole
2-[N-methyl-N-(4-(benzo[b]thien-3-yl)-butyl)-3-amino-propyl]-5,6-dimethoxy-1,3-dihydro-1-oxo-isoindole
2-[N-methyl-N-(3-(furan-2-yl)-propyl)-3-amino-propyl]-5,6-dimethoxy-1,3-dihydro-1-oxo-isoindole
2-[N-methyl-N-(3-(furan-3-yl)-propyl)-3-amino-propyl]-5,6-dimethoxy-1,3-dihydro-1-oxo-isoindole
2-[N-methyl-N-(3-(thien-2-yl)-propyl)-3-amino-propyl]-5,6-methylenedioxy-1,3-dihydro-1-oxo-isoindole
2-[N-methyl-N-(4-(thien-2-yl)-butyl)-3-amino-propyl]-5,6-methylenedioxy-1,3-dihydro-1-oxo-isoindole
2-[N-methyl-N-(5-(thien-2-yl)-pentyl)-3-amino-propyl]-5,6-methylenedioxy-1,3-dihydro-1-oxo-isoindole
2-[N-methyl-N-(3-(thien-3-yl)-propyl)-3-amino-propyl]-5,6-methylenedioxy-1,3-dihydro-1-oxo-isoindole
2-[N-methyl-N-(4-(thien-3-yl)-butyl)-3-amino-propyl]-5,6-methylenedioxy-1,3-dihydro-1-oxo-isoindole
2-[N-methyl-N-(5-(thien-3-yl)-pentyl)-3-amino-propyl]-5,6-methylenedioxy-1,3-dihydro-1-oxo-isoindole
2-[N-methyl-N-(3-(benzo[b]thien-3-yl)-propyl)-3-amino-propyl]-5,6-methylenedioxy-1,3-dihydro-1-oxo-isoindole
2-[N-methyl-N-(4-(benzo[b]thien-3-yl)-butyl)-3-amino-propyl]-5,6-methylenedioxy-1,3-dihydro-1-oxo-isoindole
2-[N-methyl-N-(3-(furan-2-yl)-propyl)-3-amino-propyl]-5,6-methylenedioxy-1,3-dihydro-1-oxo-isoindole
2-[N-methyl-N-(3-(furan-3-yl)-propyl)-3-amino-propyl]-5,6-methylenedioxy-1,3-dihydro-1-oxo-isoindole
2-[N-methyl-N-(3-(thien-2-yl)-propyl)-3-amino-propyl]-5,6-dimethyl-1,3-dihydro-1-oxo-isoindole
2-[N-methyl-N-(4-(thien-2-yl)-butyl)-3-amino-propyl]-5,6-dimethyl-1,3-dihydro-1-oxo-isoindole
2-[N-methyl-N-(5-(thien-2-yl)-pentyl)-3-amino-propyl]-5,6-dimethyl-1,3-dihydro-1-oxo-isoindole
2-[N-methyl-N-(3-(thien-3-yl)-propyl)-3-amino-propyl]-5,6-dimethyl-1,3-dihydro-1-oxo-isoindole
2-[N-methyl-N-(4-(thien-3-yl)-butyl)-3-amino-propyl]-5,6-dimethyl-1,3-dihydro-1-oxo-isoindole
2-[N-methyl-N-(5-(thien-3-yl)-pentyl)-3-amino-propyl]-5,6-dimethyl-1,3-dihydro-1-oxo-isoindole
2-[N-methyl-N-(3-(benzo[b]thien-3-yl)propyl)-3-amino-propyl]-5,6-dimethyl-1,3-dihydro-1-oxo-isoindole
2-[N-methyl-N-(4-(benzo[b]thien-3-yl)-butyl)-3-amino-propyl]-5,6-dimethyl-1,3-dihydro-1-oxo-isoindole
2-[N-methyl-N-(3-(furan-2-yl)-propyl)-3-amino-propyl]-5,6-dimethyl-1,3-dihydro-1-oxo-isoindole
2-[N-methyl-N-(3-(furan-3-yl)-propyl)-3-amino-propyl]-5,6-dimethyl-1,3-dihydro-1-oxo-isoindole
2-[N-methyl-N-(3-(thien-2-yl)-propyl)-3-amino-propyl]-5,6-dimethoxy-1-oxo-1,2,3,4-tetrahydro-isoquinoline
2-[N-methyl-N-(4-(thien-2-yl)-butyl)-3-amino-propyl]-5,6-dimethoxy-1-oxo-1,2,3,4-tetrahydro-isoquinoline
2-[N-methyl-N-(5-(thien-2-yl)-pentyl)-3-amino-propyl]-5,6-dimethoxy-1-oxo-1,2,3,4-tetrahydro-isoquinoline
2-[N-methyl-N-(3-(thien-3-yl)-propyl)-3-amino-propyl]-5,6-dimethoxy-1-oxo-1,2,3,4-tetrahydro-isoquinoline
2-[N-methyl-N-(4-(thien-3-yl)-butyl)-3-amino-propyl]-5,6-dimethoxy-1-oxo-1,2,3,4-tetrahydro-isoquinoline
2-[N-methyl-N-(5-(thien-3-yl)-pentyl)-3-amino-propyl]-5,6-methylenedioxy-1-oxo-1,2,3,4-tetrahydro-isoquinoline
2-[N-methyl-N-(3-(benzo[b]thien-3-yl)-propyl)-3-amino-propyl]-5,6-methylenedioxy-1-oxo-1,2,3,4-tetrahydro-isoquinoline
2-[N-methyl-N-(4-(benzo[b]thien-3-yl)-butyl)-3-amino-propyl]-5,6-methylenedioxy-1-oxo-1,2,3,4-tetrahydro-isoquinoline
2-[N-methyl-N-(3-(furan-2-yl)-propyl)-3-amino-propyl]-5,6-methylenedioxy-1-oxo-1,2,3,4-tetrahydro-isoquinoline
2-[N-methyl-N-(3-(furan-3-yl)-propyl)-3-amino-propyl]-5,6-methylenedioxy-1-oxo-1,2,3,4-tetrahydro-isoquinoline
2-[N-methyl-N-(3-(thien-2-yl)-propyl)-3-amino-propyl]-5,6-dimethyl-1-oxo-1,2,3,4-tetrahydro-isoquinoline
2-[N-methyl-N-(4-(thien-2-yl)-butyl)-3-amino-propyl]-5,6-dimethyl-1-oxo-1,2,3,4-tetrahydro-isoquinoline
2-[N-methyl-N-(5-(thien-2-yl)-pentyl)-3-amino-propyl]-5,6-dimethyl-1-oxo-1,2,3,4-tetrahydro-isoquinoline 2-[N-methyl-N-(3-(thien-3-yl)-propyl)-3-amino-propyl]-5,6-dimethyl-1-oxo-1,2,3,4-tetrahydro-isoquinoline 2-[N-methyl-N-(4-(thien-3-yl)-butyl)-3-amino-propyl]-5,6-dimethyl-1-oxo-1,2,3,4-tetrahydro-isoquinoline 2-[N-methyl-N-(5-(thien-3-yl)-pentyl)-3-amino-propyl]-5,6-dimethyl-1-oxo-1,2,3,4-tetrahydro-isoquinoline 2-[N-methyl-N-(3-(benzo[b]thien-3-yl)-propyl)-3-amino-propyl]-5,6-dimethyl-1-oxo-1,2,3,4-tetrahydro-isoquinoline 2-[N-methyl-N-(4-(benzo[b]thien-3-yl)-butyl)-3-amino-propyl]-5,6-dimethyl-1-oxo-1,2,3,4-tetrahydro-isoquinoline 2-[N-methyl-N-(3-(furan-2-yl)-propyl)-3-amino-propyl]-5,6-dimethyl-1-oxo-1,2,3,4-tetrahydro-isoquinoline 2-[N-methyl-N-(3-(furan-3-yl)-propyl)-3-amino-propyl]-5,6-dimethyl-1-oxo-1,2,3,4-tetrahydro-isoquinoline 2-[N-methyl-N-(2-(thien-2-yl)-ethyl)-3-amino-propyl]-5,6-dimethoxy-1,3-dihydro-1-thioxo-isoindole 2-[N-methyl-N-(3-(thien-3-yl)-propyl)-3-amino-propyl]-5,6-dimethoxy-1,3-dihydro-1-thioxo-isoindole 2-[N-methyl-N-(4-(thien-2-yl)-butyl)-3-amino-propyl]-5,6-dimethoxy-1,3-dihydro-1-thioxo-isoindole 2-[N-methyl-N-(2-(thien-3-yl)-ethyl)-3-amino-propyl]-5,6-dimethoxy-1,3-dihydro-1-thioxo-isoindole 2-[N-methyl-N-(2-(benzo[b]thien-3-yl)-ethyl)-3-amino-propyl]-5,6-dimethoxy-1,3-dihydro-1-thioxo-isoindole 2-[N-methyl-N-(2-(thien-2-yl)-ethyl)-3-amino-propyl]-5,6-methylenedioxy-1,3-dihydro-1-thioxo-isoindole 2-[N-methyl-N-(3-(thien-2-yl)-propyl)-3-amino-propyl]-5,6-methylenedioxy-1,3-dihydro-1-thioxo-isoindole 2-[N-methyl-N-(4-(thien-2-yl)-butyl)-3-amino-propyl]-5,6-methylenedioxy-1,3-dihydro-1-thioxo-isoindole 2-[N-methyl-N-(2-(thien-3-yl)-ethyl)-3-amino-propyl]-5,6-methylenedioxy-1,3-dihydro-1-thioxo-isoindole 2-[N-methyl-N-(2-(benzo[b]thien-3-yl)-ethyl)-3-amino-propyl]-5,6-methylenedioxy-1,3-dihydro-1-thioxo-isoindole 2-[N-methyl-N-(2-(thien-2-yl)-ethyl)-3-amino-propyl]-5,6-dimethoxy-1,3-dihydro-isoindole 2-[N-methyl-N-(3-(thien-2-yl)-propyl)-3-amino-propyl]-5,6-dimethoxy-1,3-dihydro-isoindole 2-[N-methyl-N-(4-(thien-2-yl)-butyl)-3-amino-propyl]-5,6-dimethoxy-1,3-dihydro-isoindole 2-[N-methyl-N-(2-(thien-3-yl)-ethyl)-3-amino-propyl]-5,6-dimethoxy-1,3-dihydro-isoindole 2-[N-methyl-N-(2-(benzo[b]thien-3-yl)-ethyl)-3-amino-propyl]-5,6-dimethoxy-1,3-dihydro-isoindole 2-[N-methyl-N-(2-(thien-2-yl)-ethyl)-3-amino-propyl]5,6-dimethyl-1,3-dihydro-1-thioxo-isoindole 2-[N-methyl-N-(3-(thien-2-yl)-propyl)-3-amino-propyl]-5,6-dimethyl-1,3-dihydro-1-thioxo-isoindole 2-[N-methyl-N-(4-(thien-2-yl)-butyl)-3-amino-propyl]-5,6-dimethyl-1,3-dihydro-1-thioxo-isoindole 2-[N-methyl-N-(2-(thien-3-yl)-ethyl)-3-amino-propyl]-5,6-dimethyl-1,3-dihydro-1-thioxo-isoindole 2-[N-methyl-N-(2-(benzo[b]thien-3-yl)-ethyl)-3-amino-propyl]-5,6-dimethyl-1,3-dihydro-1-thioxo-isoindole 2-[N-methyl-N-(2-(thien-2-yl)-ethyl)-3-amino-propyl]-5,6-methylenedioxy-1,3-dihydro-isoindole 2-[N-methyl-N-(3-(thien-2-yl)-propyl)-3-amino-propyl]-5,6-methylenedioxy-1,3-dihydro-isoindole 2-[N-methyl-N-(4-thien-2-yl)-butyl)-3-amino-propyl]-5,6-methylenedioxy-1,3-dihydro-isoindole 2-[N-methyl-N-(2-(thien-3-yl)-ethyl)-3-amino-propyl]-5,6-methylenedioxy-1,3-dihydro-isoindole 2-[N-methyl-N-(2-(benzo[b]thien-3-yl)-ethyl)-3-amino-propyl]-5,6-methylenedioxy-1,3-dihydro-isoindole 2-[N-methyl-N-(2-(thien-2-yl)-ethyl)-3-amino-propyl]-5,6-dimethyl-1,3-dihydro-isoindole 2-[N-methyl-N-(3-(thien-2-yl)-propyl)-3-amino-propyl]-5,6-dimethyl-1,3-dihydro-isoindole 2-[N-methyl-N-(4-(thien-2-yl)-butyl)-3-amino-propyl]-5,6-dimethyl-1,3-dihydro-isoindole 2-[N-methyl-N-(2-(thien-3-yl)-ethyl)-3-amino-propyl]-5,6-dimethyl-1,3-dihydro-isoindole 2-[N-methyl-N-(2-(benzo[b]thien-3-yl)-ethyl)-3-amino-propyl]-5,6-dimethyl-1,3-dihydro-isoindole 2-[N-ethyl-N-(2-(thien-2-yl)-ethyl)-3-amino-propyl]-5,6-dimethoxy-1,3-dihydro-1-oxo-isoindole 2-[N-(2-(thien-2-yl)-ethyl)-3-amino-propyl]-5,6-dimethoxy-1,3-dihydro-1-oxo-isoindole 2-[N-(2-(thien-3-yl)-ethyl)-3-amino-propyl]-5,6-dimethoxy-1,3-dihydro-1-oxo-isoindole 2-[N-methyl-N-(2-(thien-2-yl)-ethyl)-3-amino-propyl]-1,3-dihydro-1-oxo-isoindole 2-[N-methyl-N-(2-(thien-3-yl)-ethyl)-3-amino-propyl]-1,3-dihydro-1-oxo-isoindole 2-[N-methyl-N-(thien-2-yl)-methyl)-3-amino-propyl]-1,3-dihydro-1-oxo-isoindole 2-[N-methyl-N-(2-(thien-2-yl)-ethyl)-2-amino-ethyl]-1,3-dihydro-1-oxo-isoindole 2-[N-methyl-N-(2-(thien-2-yl)-ethyl)-4-amino-butyl]-1,3-dihydro-1-oxo-isoindole However, the preferred compounds of the present invention are the compounds of general formula

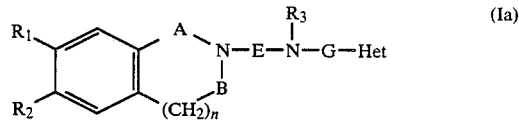

(Ia)

wherein n represents the number 0 or 1,

A represents a methylene or carbonyl group or, if B represents a methylene group, A may represent a thiocarbonyl group, B represents a methylene or carbonyl group, E represents an n-propylene group, G represents a methylene, ethylene, n-propylene, n-butylene or n-pentylene group, $R_1$ and $R_2$, which may be identical or different, represent hydrogen atoms, methyl or methoxy groups or $R_1$ and $R_2$ together represent a methylenedioxy group, $R_3$ represents a hydrogen atom, a methyl or allyl group and Het represents a pyrrol-2-yl, pyrrol-3-yl, N-methylpyrrol-2-yl, N-methyl-pyrrol-3-yl, furan-2-yl, furan-3-yl, benzo[b]furan-2-yl, benzo[b]furan-3-yl, 7-methylbenzo[b]furan-3-yl, 6-methoxy-benzo[b]furan-3-yl, 5-methoxy-3-phenyl-benzo[b]furan-2-yl, thien-2-yl, thien-3-yl, 5-methyl-thien-2-yl, 2,5-dimethyl-thien-3-yl, 5-bromo-thien-2-yl, benzo[b]thien-2-yl, benzo[b]thien-3-yl, 6-hydroxy-benzo[b]thien-3-yl, 6-methoxy-benzo[b]thien-3-yl, 5,6-dimethoxy-benzo[b]thien-3-yl, 2,5-dimethyl-benzo[b]thien-3-yl, 5-methoxy-benzo[b]thien-2-yl, 6-methoxy-benzo[b]thien-2-yl, 6-methylmercapto-benzo[b]thien-3-yl, 6-methylsulphinyl-benzo[b]thien-3-yl, 6-methylsulphonyl-benzo[b]thien-3-yl, 6-methylsulphonyloxy-benzo[b]thien-3-yl, 6-ethoxy-carbonylmethoxy-benzo[b]thien-3-yl, 6-carboxy-methoxy-benzo[b]thien-3-yl, 6-dimethylamino-benzo[b]thien-3-yl, 6-methylsulphonylamino-benzo[b]thien-3-yl, 6- acetamino-benzo[b]thien-3-yl, benzo[b]thien-4-yl, pyrazol-1-yl, pyrazol-3-yl, 1,5-dimethyl-pyrazol-3-yl, 1-methyl-imidazol-4-yl, 2-(3,4-dimethoxy-phenyl)-imidazol-4(5)-yl, benzo[d]imidazol-1-yl, 2-benzyl-benzo[d]imidazol-1-yl, oxazol-4-yl, oxazol-5-yl, isoxazol-3-yl, 3-methyl-isoxazol-5-yl, 4-methyl-thiazol-5-yl, pyridin-2-yl, pyridin-3-yl, pyridin-4-yl, pyridin-3-yl-N-oxide, 4-nitro-pyridin-2-yl, 4-amino-pyridin-2-yl, 4-acetylamino-pyridin-2-yl, 4-carbamoylamino-pyridin-2-yl, 4-N-methyl-carbamoylamino-pyridin-2-yl, indol-2-yl, indol-3-yl, 5-methyl-indol-3-yl, 5-methoxy-indol-3-yl, N-methyl-indol-3-yl, 6,7-dimethoxy-quinolin-4-yl, 6,7-dimethoxy-isoquinolin-4-yl or 6,7-dimethoxy-isoquinolin-4-yl-N-oxide group, and the acid addition salts thereof, particularly the physiologically acceptable acid addition salts thereof with inorganic or organic acids.

However, particularly preferred compounds of formula Ia above are those wherein

A, B, E, G and n are defined as hereinbefore, $R_1$ and $R_2$, which may be identical or different, represent methyl or methoxy groups or $R_1$ and $R_2$ represent a methylenedioxy group, $R_3$ represents a hydrogen atom or a methyl group and Het represents a thienyl, furanyl, pyridinyl, pyrid-3-yl-N-oxide, benzo[b]furan-2-yl, benzo[b]furan-3-yl, benzo[b]thien-2-yl, benzo[b]thien-3-yl, indol-3-yl or 6,7-dimethoxy-isoquinolin-4-yl group, and the acid addition salts thereof, particularly the physiologically acceptable acid addition salts thereof with inorganic or organic acids.

According to the invention, the new compounds are obtained by the following methods:

(a) Reaction of a compound of general formula

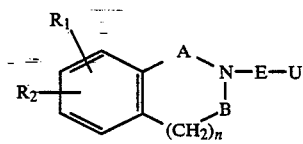
(II)

with a compound of general formula

V—G—Het (III)

wherein $R_1$, $R_2$, A, B, E, G, n and Het are defined as hereinbefore, but wherein A or B cannot represent a thiocarbonyl group, one of the groups U or V represents the $R_3'$—NH— group, wherein $R_3'$ represents a protecting group for an amino group or has the meanings given for $R_3$ hereinbefore, and the other group U or V represents a nucleophilically exchangeable group such as a halogen atom or a sulphonyloxy group, e.g. a chlorine, bromine or iodine atom, a methanesulphonyloxy, benzenesulphonyloxy, p-toluenesulphonyloxy or ethoxysulphonyloxy group, and any protecting group used is subsequently split off if necessary.

Examples of protecting groups for an amino or alkylamino group include the acetyl, benzoyl, ethoxycarbonyl or benzyl groups.

The reaction is conveniently carried out in a solvent or mixture of solvents such as acetone, diethylether, methylformamide, dimethylformamide, dimethylsulphoxide, benzene, toluene, chlorobenzene, tetrahydrofuran, benzene/tetrahydrofuran, dioxane or in an excess of the compounds of general formula II or III used, optionally in the presence of an acid-binding agent, e.g. an alkoxide such as potassium tert.-butoxide, an alkali metal hydroxide such as sodium or potassium hydroxide, an alkali metal carbonate such as potassium carbonate, an alkali metal amide such as sodium amide, an alkali metal hydride such as sodium hydride, a tertiary organic base such as triethylamine or pyridine, whilst the latter may simultaneously serve as solvent, or a reaction accelerator such as potassium iodide, depending on the reactivity of the nucleophilically exchangeable group, conveniently at temperatures between 0° and 150° C., preferably at temperatures between 50° and 120° C., e.g. at the boiling temperature of the solvent used. The reaction can, however, be carried out without a solvent. The reaction is however preferably carried out in the presence of a tertiary organic base or an excess of the amines of general formula II or III used.

The optional subsequent splitting off of any protecting group used is preferably carried out hydrolytically in an aqueous solvent, e.g. in water, isopropanol/water, tetrahydrofuran/water or dioxane/water, in the presence of an acid such as hydrochloric or sulphuric acid or in the presence of an alkali metal base such as sodium hydroxide or potassium hydroxide at temperatures of between 0° and 100° C., preferably at the boiling temperature of the reaction mixture. However, a benzyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures of between 0° and 50° C., but preferably at ambient temperature, under a hydrogen pressure of from 1 to 7 bar, preferably from 3 to 5 bar.

(b) Reaction of a compound of general formula

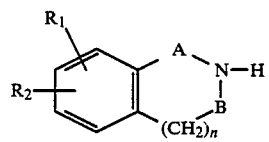
(IV)

wherein $R_1$, $R_2$, A, B and n are defined hereinbefore, but A or B cannot represent a thiocarbonyl group, with a compound of general formula

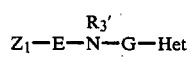
(V)

wherein

E, G and Het are as defined hereinbefore, $R'_3$ represents a protecting group for an amino group or has the meanings given for $R_3$ hereinbefore and $Z_1$ represents a nucleophilically exchangeable group such as a halogen atom or a sulphonyloxy group, e.g. a chlorine, bromine or iodine atom, the methanesulphonyloxy, p-toluenesulphonyloxy or ethoxysulphonyloxy group, and subsequently if necessary splitting off any protecting group used.

Examples of protecting groups for an amino or alkylamino group include the acetyl, benzoyl, ethoxycarbonyl or benzyl group.

The reaction is conveniently carried out in a solvent or mixture of solvents such as methylformamide, dimethylformamide, dimethylsulfoxide, benzene, chlorobenzene, tetrahydrofuran, benzene/tetrahydrofuran or dioxane in the presence of an acid binding agent, e.g. an alkoxide such as potassium tert.butoxide, an alkali metal hydroxide such as sodium or potassium hydroxide, an alkali metal carbonate such as potassium carbonate, an alkali metal amide such as sodium amide or an alkali metal hydride such as sodium hydride, conveniently at temperatures of between 0° and 150° C., preferably at temperatures of between 0° and 50° C.

The optional subsequent splitting off of any protecting group used is preferably carried out hydrolytically in an aqueous solvent, e.g. in water, isopropanol/water, tetrahydrofuran/water or dioxane/water, in the presence of an acid such as hydrochloric or sulphuric acid or in the presence of an alkali metal base such as sodium hydroxide or potassium hydroxide at temperatures of between 0° and 100° C., preferably at the boiling temperature of the reaction mixture. However, a benzyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures of between 0° and 50° C., but preferably at ambient temperature, under a hydrogen pressure of from 1 to 7 bar, preferably from 3 to 5 bar.

(c) Reductive amination of a compound of general formula

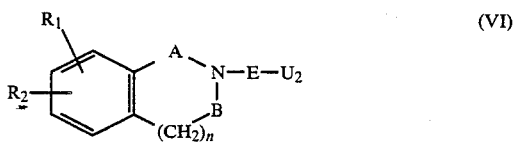

(VI)

in the presence of a compound of general formula $$V_2-G-\text{Het} \qquad (VII)$$

wherein $R_1$, $R_2$, A, B, E, G, Het and n are defined as hereinbefore, one of the groups $U_2$ or $V_2$ represents an $R_3$—NH— group, wherein $R_3$ is defined as hereinbefore, and the other group $U_2$ or $V_2$ together with a hydrogen atom of the adjacent carbon atom of the group G or E, wherein E and G are both defined as hereinbefore, represents an oxygen atom.

The reduction is carried out in a suitable solvent such as methanol, ethanol, diethylether, tetrahydrofuran, dioxane, ethyl acetate or ethanol/ethyl acetate with a metal hydride such as lithium aluminium hydride, diborane, sodium cyanoborohydride or borane/dimethylsulphide, but preferably with sodium borohydride, or with hydrogen in the presence of a hydrogenation catalyst such as platinum, palladium/charcoal or Raney nickel at a hydrogen pressure of 1 to 5 bar or with hydrazine in the presence of a hydrogenation catalyst such as platinum, palladium/charcoal or Raney nickel, at temperatures of between 0° and 50° C., preferably at ambient temperature.

During the reduction with a complex metal hydride such as lithium aluminium hydride, diborane or borane/dimethylsulphide, a carbonyl function present in the groups A and/or B may be reduced to form a methylene group or during catalytic hydrogenation any double bond present in the group $R_3$ may be reduced. Furthermore, a thiocarbonyl group present in the groups A or B or a carbonyl function present in the group Het may also be reduced at the same time.

(d) Reduction of an acid amide of general formula

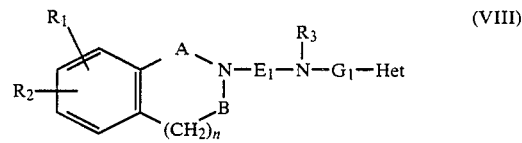

(VIII)

wherein $R_1$ to $R_3$, A, B, Het and n are defined as hereinbefore, one of the groups $E_1$ or $G_1$ has the meanings given for E or G hereinbefore and the other group $E_1$ or $G_1$ also has the meanings given for E or G hereinbefore, but a methylene group adjacent to a nitrogen atom must be replaced by a carbonyl group.

The reduction is preferably carried out in a suitable solvent such as methanol, ethanol, diethylether or tetrahydrofuran with a suitable reducing agent, e.g. with a metal hydride such as lithium aluminium hydride, diborane, borane/dimethylsulphide or sodium cyanoborohydride, but preferably with diborane in tetrahydrofuran at between 0° and 40° C., preferably at ambient temperature.

In the reduction with a complex metal hydride such as lithium aluminium hydride, diborane or borane/-dimethyl- sulphide, a carbonyl function present in the groups A and/or B may be reduced to form a methylene group. Moreover, a thiocarbonyl group present in the groups A or B or a carbonyl function present in the group Het may also be reduced at the same time.

(e) In order to prepare compounds of general formula I wherein A or B represents a thiocarbonyl group: reaction of a compound of general formula

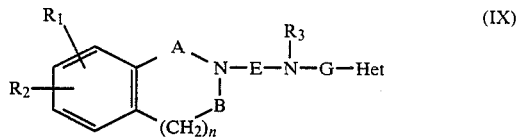

(IX)

wherein $R_1$ to $R_3$, A, B, E, G, Het and n are defined as hereinbefore, but one of the groups A or B must represent a carbonyl group and the other group A or B must represent a methylene group, with a sulphurizing agent.

The reaction is carried out with a sulphurising agent such as phosphorus pentasulphide or 2,4-bis(4-methoxyphenyl)-1,3-dithia-2,4-diphosphetan-2,4-disulphide conveniently in a solvent such as toluene or xylene at temperatures of between 50° and 150° C., e.g. at the boiling temperature of the reaction mixture.

(f) In order to prepare compounds of general formula I wherein A and B each represent a —CH$_2$— group: reduction of a compound of general formula

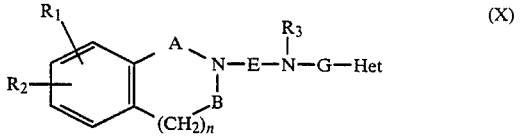

(X)

wherein $R_1$ to $R_3$, E, G, Het and n are defined as hereinbefore, one of the radicals A' or B' represents a carbonyl or thiocarbonyl group and the other of the radicals A' or B' represents a methylene, carbonyl or thiocarbonyl group.

The reduction is preferably carried out with a metal hydride such as lithium aluminium hydride or diborane or with a complex of borane and a thioether, e.g. with borane-dimethylsulphide complex, in a suitable solvent such as diethylether or tetrahydrofuran at temperatures of between 0° and 50° C., but preferably at temperatures of between 10° and 25° C. Moreover, B or a carbonyl function present in the group Het may be reduced at the same time.

(g) In order to prepare compounds of general formula I wherein A represents a methylene group: reduction of a compound of general formula

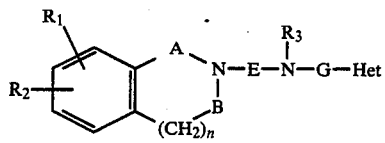

wherein $R_1$ to $R_3$, A, B, E, G, Het and n are defined as hereinbefore.

The reduction is preferably carried out in a suitable solvent such as glacial acetic acid, water, ethanol or water/glacial acetic acid, conveniently with nascent hydrogen, e.g. in the presence of zinc/glacial acetic acid, tin/hydrochloric acid or tin(II) chloride/ hydrochloric acid, or with catalytically activated hydrogen at temperatures of between 0° and 150° C., preferably at temperatures of between 20° and 125° C. Any double bond present in the group $R_3$ or any nitro group contained in the group Het may also be reduced at the same time.

If they have at least one chiral centre, the compounds of general formula I obtained can be resolved by conventional methods into their diastereomers, for example by column chromatography, and into their enantiomers, for example by column chromatography on a chiral phase or by crystallization with optically active acids, e.g. with D- or L-monomethyltartaric acid, D- or L-diacetyltartaric acid, D- or L-tartaric acid, D- or L-lactic acid or D- or L-camphoric acid.

The compounds of general formula I obtained may also be converted into the acid addition salts thereof, particularly for pharmaceutical use into the physiologically acceptable acid addition salts thereof with inorganic or organic acids. Suitable acids include, for example, hydrochloric, hydrobromic, sulphuric, phosphoric, acetic, lactic, citric, tartaric, succinic, maleic and fumaric acids.

The compounds of general formulae II to XI used as starting materials are known from the literature in some cases or may be obtained using methods known per se.

Thus, for example, a compound of general formula

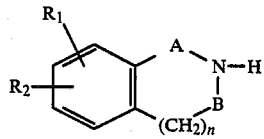

(wherein $R_1$, $R_2$ and n are defined as hereinbefore, A represents a carbonyl group and B represents a methylene group) used as starting material may be prepared by cyclizing a corresponding compound of general formula

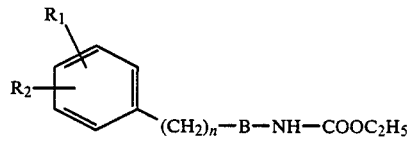

with polyphosphoric acid or a compound of general formula IV wherein $R_1$, $R_2$ and n are defined as hereinbefore, A and B each represent a CO group, may be prepared by cyclizing a corresponding diamide. A compound of general formula IV thus obtained may subsequently be converted into a corresponding methylene compound by reduction.

The compounds of general formulae II, VI and VIII–XI used as starting materials are obtained by reaching a compound of general formula IV with a corresponding halogen compound or a corresponding dihalogen compound, optionally followed by reaction with a corresponding amine.

As already mentioned hereinbefore, the new compounds of general formula I and the physiologically acceptable acid addition salts thereof with inorganic or organic acids have valuable pharmacological properties, particularly a lowering effect on heart rate and the effect of reducing the $O_2$ requirement of the heart, together with a mild hypotensive activity and a positive inotropic activity.

For example, the following compounds:

A = 2-[N-methyl-N-(2-(benzo[b]thien-3-yl)-ethyl)-3-amino-propyl]-6,7-dimethoxy-1-oxo-1,2,3,4-tetrahydro-isoquinoline hydrochloride, B = 2-[N-methyl-N-(2-(thien-3-yl)-ethyl)-3-amino-propyl]-5,6-dimethoxy-1,3-dihydro-1-oxo-isoindole dihydrochloride and C = 2-[N-methyl-N-(2-(benzo[b]thien-3-yl)-ethyl)-3-amino-propyl]-5,6-dimethoxy-1,3-dihydro-1-oxo-isoindole dihydrochloride were tested for their biological properties as follows:

Determination of the positive inotropic and heart rate lowering activity on isolated guinea-pig auricles:

The positive inotropic activity was determined as the effect on the contractility of isolated guinea-pig auricles. Freshly prepared guinea-pig auricles were transferred into a 65 ml organ bath filled with Krebs-Henseleit solution (1.8 mM Ca++) at 37° C. Carbogen (95% oxygen and 5% carbon dioxide) was bubbled through the bath. The auricles were stimulated electrically at a rate of 1 Hz; their pre-extension was 10 mN. The contractions were recorded isometrically on a Grass polygraph. After an equilibration period of 60 minutes the test substances were administered so as to obtain a final concentration of $10^{-5}$M.

The effect on heart rate was determined on spontaneously beating guinea-pig auricles in a test arrangement otherwise identical to that described above.

The following Table contains the averages of two measurements in each case:

| Substance | Increase in force of contractions in % | Change in heart rate in % |
|---|---|---|
| A | +54 | −21 |
| B | +127 | −17 |
| C | +61 | −41 |

In view of their pharmacological properties, the compounds prepared according to the invention are suitable for the treatment of cardiac insufficiency and for the prevention and treatment of ischaemic heart disease.

The dosage required to achieve this effect is conveniently from 0.2 to 5 mg/kg of body weight, preferably from 0.5 to 2 mg/kg of body weight, once or twice a day. The compounds of general formula I and the physiologically acceptable acid addition salts thereof with inorganic or organic acids produced according to the invention may be incorporated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, carboxymethylcellulose or fatty substances such as hart fat or suitable mixtures thereof, to produce conventional galenic preparations such as tablets, coated tablets, capsules, powders, suspensions, drops, ampoules, syrups or suppositories.

The following Examples are intended to illustrate the invention:

EXAMPLE 1

2-[N-Methyl-N-(2-(thien-2-yl)-ethyl)-3-amino-propyl]-6,7-dimethoxy-1-oxo-1,2,3,4-tetrahydro-isoquinoline hydrochloride 0.85 g (3.0 mmol) of 2-(N-methyl-3-amino-propyl)-6,7-dimethoxy-1-oxo-1,2,3,4-tetrahydro-isoquinoline, 0.60 g (3.1 mmol) of 2-(2-bromo-ethyl)-thiophene and 5 ml of triethylamine are dissolved in 10 ml of dry dimethylformamide and heated to 100° C. for 4 hours. The reaction mixture is evaported down in vacuo and the residue is dissolved in a mixture of 2 molar sodium hydroxide solution and methylene chloride. The organic phase is separated off, washed with saturated saline solution, dried over sodium sulphate and evaporated down in vacuo. The crude product is purified by column chromatography (adsorption agent: silica gel, eluant: methylene chloride/methanol=10/1). The hydrochloride is precipitated from a solution in methanol with ethereal hydrochloric acid and then crystallized from acetone.

Yield: 0.40 g (31% of theory),

Melting point: 150°–151° C.

Calculated: C 59.35 H 6.88 N 6.59 Cl 8.34 S 7.54. Found C 59.40 H 6.73 N 6.29 Cl 8.11 S 7.59.

$R_f$ value (base): 0.42 (silica gel, methylene chloride in an $NH_3$ atmosphere).

EXAMPLE 2

2-[Methyl-N-(2-(indol-3-yl)-ethyl)-3-amino-propyl]-5,6-dimethoxy-phthalimide 1.15 g (3.5 mmol) of 2-(3-bromo-propyl)-5,6-dimethoxy-phthalimide are dissolved in 15 ml of absolute dimethylformamide with gentle heating. After the addition of 0.61 g (3.5 mmol) of 3-(2-methylaminoethyl)-indole and 15 ml of triethylamine the mixture is refluxed for 8 hours. The reaction mixture is evaporated to dryness in vacuo and distributed between 8% sodium hydroxide and methylene chloride. The organic phase is washed three times with 10 ml of water, separated off, dried with sodium sulphate and evaporated down. After purification over a silica gel column using methylene chloride/methanol as eluant, 0.9 g of a yellow oil are obtained.

Yield: 0.90 g (61% of theory),

Calculated: C 68.39 H 6.46 N 9.97. Found: C 68.28 H 6.50 N 9.91.

$R_f$ value: 0.47 (silica gel, methylene chloride/methanol=9/1).

EXAMPLE 3

2-[N-Methyl-N-(2-(thien-2-yl)-ethyl)-3-amino-propyl]-5,6-dimethoxy-1,3-dihydro-1-oxo-isoindole hydrochloride 1.5 g (3.9 mmol) of 2-[N-methyl-N-(2-(thien-2-yl)-ethyl)-3-amino-propyl]-5,6dimethoxy-phthalimide and 1.5 g (23 mmol) of zinc powder are refluxed for 1.5 hours in 15 ml of glacial acetic acid. The mixture is filtered whilst still hot to remove the insoluble matter and the residue is extracted twice, each time with 8 ml of hot glacial acetic acid. The collected acetic acid phases are evaporated down in vacuo and the residue is distributed in 8% sodium hydroxide solution and methylene chloride. The organic phase is washed with water, separated off, dried over sodium sulphate and evaporated down in vacuo. The purification of the crude product over a silica gel column using methylene chloride/methanol as eluant yields 1.1 g (75% of theory) of a yellow oil. It is dissolved in a little absolute methanol and the hydrochloride is precipitated with ethereal hydrochloric acid.

Yield: 1.0 g (62% of theory),

Melting point: 211°–212° C.

Calculated: C 58.45 H 6.62 N 6.82 Cl 8.63 S 7.80. Found: C 58.68 H 6.80 N 7.00 Cl 8.84 S 7.59.

$R_f$ value (base): 0.55 (silica gel, methylene chloride/methanol=9/1).

EXAMPLE 4

2-[N-Methyl-N-(3-(pyrid-4-yl)-propyl)-3-amino-propyl]-6,7-methylenedioxy-1-oxo-1,2,3,4-tetrahydro-isoquinoline-dihydrochloride 1.3 g (5 mmol) of 2-(2-formyl-ethyl)-6,7-methylenedioxy-1-oxo-1,2,3,4-tetrahydro-isoquinoline and 0.75 g (5 mmol) of 4-(3-methylamino-propyl)-pyridine are hydrogenated in 50 ml of ethanol in the presence of 0.2 g of 10% palladium on activated charcoal at 70° C. and 5 bar until the calculated quantity of hydrogen has been absorbed. The catalyst is filtered off and the filtrate is evaporated to dryness in vacuo. The dihydrochloride is precipitated with ethereal hydrochloric acid from a solution in acetone and is then recrystallized from acetone/ether.

Yield: 1.7 g (74% of theory),

Melting point: 86°–94° C.

Calculated: C 58.15 H 6.43 N 9.24 Cl 15.60. Found: C 57.91 H 6.31 N 9.15 Cl 15.36.

The reduction may also be carried out with sodium borohydride in ethanol at ambient temperature or at boiling point.

EXAMPLE 5

2-[N-Methyl-N-(3-(pyrid-4-yl)-propyl)-3-amino-propyl]-5,6-dimethyl-1,3-dihydro-isoindole dihydrochloride A mixture of 2.0 g (5.7 mmol) of 2-[methyl-N-(3-pyrid-4-yl)-propyl)-3-amino-propyl]-5,6-dimethyl-1,3-dihydro-1-oxo-isoindole and 0.43 g (11.4 mmol) of lithium aluminium hydride in 45 ml of absolute tetrahydrofuran is refluxed for 1 hour. After cooling, the mixture is decomposed with 0.57 ml of water, 0.57 ml of 10% sodium hydroxide solution and 1.71 ml of water, then suction filtered and the filtrate is evaporated down in vacuo. The residue obtained is purified over 180 g of aluminium oxide (neutral, activity II-III) with methylene chloride and then with increasing amounts of ethanol (up to 3%). The dihydrochloride is precipitated with ethereal hydrochloric acid from a solution in acetone.

Yield: 1.85 g (80% of theory),
Melting point: 239°-240° C.
Calculated: C 64.37 H 8.10 N 10.23 Cl 17.27. Found: C 64.20 H 8.37 N 10.07 Cl 17.36.

EXAMPLE 6

2-[N-Methyl-N-(2-(6,7-dimethoxy-isoquinolin-4-yl)-ethyl)-3-amino-propyl]-6,7-dimethoxy-1-oxo-1,2,3,4-tetrahydro-isoquinoline dihydrochloride (a)
2-[N-Methyl-N-(2-(6,7-dimethoxy-isoquinolin-4-yl)-acetyl)-3-amino-propyl]-6,7-dimethoxy-1-oxo-1,2,3,4-tetrahydro-isoquinoline hemihydrate 3.2 g (20 mmol) of N,N'-carbonyl-diimidazole are added to a solution of 4.9 g (17 mmol) of 6,7-dimethoxy-isoquinolin-4-yl-acetic acid in 100 ml of dimethylformamide. After about 30 minutes 4.8 g (17 mmol) of 2-(3-methylamino-propyl)-6,7-dimethoxy-1-oxo-1,2,3,4-tetrahydro-isoquinoline are added and the mixture is stirred for 2 hours at ambient temperature. The solvent is evaporated off in vacuo and the residue remaining is dissolved in a mixture of 2 molar sodium hydroxide solution and methylene chloride. The organic phase is washed with water, dried over magnesium sulphate and evaporated down in vacuo.

Yield: 5.3 g (63% of theory),
Melting point: 80°-85° C.
Calculated: C 65.10 H 6.63 N 8.13. Found: C 64.90 H 6.63 N 8.15.

(b)
2-[N-Methyl-N-(2-(6,7-dimethoxy-isoquinolin-4-yl)-ethyl)-3-amino-propyl]-6,7-dimethoxy-1-oxo-1,2,3,4-tetrahydro-isoquinoline dihydrochloride To a solution of 4.1 (8 mmol) of 2-[N-methyl-N-(2-(6,7-dimethoxy-isoquinolin-4-yl)-acetyl)-3-amino-propyl]-6,7-dimethoxy-1-oxo-1,2,3,4-tetrahydro-isoquinoline hemihydrate in 250 ml of tetrahydrofuran are added 12 ml of 1 molar borane-tetrahydrofuran complex in tetrahydrofuran and whilst the mixture is stirred at ambient temperature 1.5 ml (12 mmol) of boron trifluoride-diethyl-etherate complex are added dropwise. After 3 hours' reaction, 15 ml of 6 molar hydrochloric acid are added dropwise, the mixture is refluxed for 0.5 hours and solvent is then evaporated off in vacuo. The aqueous portion remaining is made alkaline with 2 molar sodium hydroxide solution and then extracted with methylene chloride. The organic phase is washed with water, dried over sodium sulphate, evaporated down in vacuo and purified over a silica gel column (0.063-0.2 mm) with methylene chloride and then with increasing amounts of ethanol (up to 5%). The dihydrochloride is precipitated with ethereal hydrochloric acid from a solution in acetone and is then recrystallized from acetone.

Yield: 0.45 g (10% of theory),
Melting point: 158°-169° C.
Calculated: C 59.36 H 6.58 N 7.42 Cl 12.52. Found: C 59.20 H 6.60 N 7.27 Cl 12.22.

The reduction may also be carried out with lithium aluminium hydride in ether or tetrahydrofuran at reflux temperature.

EXAMPLE 7

2-[N-Methyl-N-(4-(thien-2-yl)-butyl)-3-amino-propyl]-6,7-dimethoxy-1-oxo-1,2,3,4-tetrahydro-isoquinoline-hydrochloride Prepared from 2-(N-methyl-3-amino-propyl)-6,7-dimethoxy-1-oxo-1,2,3,4-tetrahydro-isoquinoline and 2-(4-bromo-butyl)-thiophene analogously to Example 1.

Yield: 64% of theory,
Melting point: 115°-120° C.
Calculated: C 60.98 H 7.34 N 6.18 Cl 7.83 S 7.08. Found: C 60.70 H 7.44 N 5.96 Cl 8.15 S 7.03.

$R_f$ value: 0.29 (silica gel, methylene chloride in an $NH_3$ atmosphere).

EXAMPLE 8

2-[N-Methyl-N-(2-(benzo[b]furan-2-yl)-ethyl)-3-amino-propyl]-6,7-dimethoxy-1-oxo-1,2,3,4-tetrahydro-isoquinoline hydrochloride Prepared from 2-(N-methyl-3-amino-propyl)-6,7-dimethoxy-1-oxo-1,2,3,4-tetrahydro-isoquinoline and 2-(2-chloro-ethyl)-benzo[b]furan analogously to Example 1.

Yield: 24% of theory,
Melting point: 180°-184° C.
Calculated: C 65.42 H 6.81 N 6.10 Cl 7.72. Found: C 65.40 H 6.80 N 5.92 Cl 7.98.

EXAMPLE 9

2-[N-Methyl-N-(2-(benzo[b]thien-3-yl)-ethyl)-3-amino-propyl]-6,7-dimethoxy-1-oxo-1,2,3,4-tetrahydro-isoquinoline hydrochloride Prepared from 2-(N-methyl-3-amino-propyl)-6,7-dimethoxy-1-oxo-1,2,3,4-tetrahydro-isoquinoline and 3-(2-methylsulphonyloxy-ethyl)-benzo[b]thiophene analogously to Example 1.

Yield: 38% of theory,
Calculated: C 63.21 H 6.58 N 5.90 Cl 7.46 S 6.75. Found: C 63.10 H 6.47 N 5.86 Cl 7.55 S 6.88.

$R_f$ value: 0.37 (silica gel, methylene chloride in an $NH_3$ atmosphere).

EXAMPLE 10

2-[N-Methyl-N-(2-(thien-3-yl)-ethyl)-3-amino-propyl]-6,7-dimethoxy-1-oxo-1,2,3,4-tetrahydro-isoquinoline hydrochloride Prepared from 2-(N-methyl-3-amino-propyl)-6,7-dimethoxy-1-oxo-1,2,3,4-tetrahydro-isoquinoline and 3-(2-bromo-ethyl)-thiophene analogously to Example 1.

Yield: 34% of theory,
Calculated: C 59.35 H 6.88 N 6.59 Cl 8.34 S 7.54. Found: C 59.47 H 6.77 N 6.57 Cl 8.59 S 7.37.

$R_f$ value: 0.34 (silica gel, methylene chloride in an $NH_3$ atmosphere).

EXAMPLE 11

2-[N-Methyl-N-(2-(indol-3-yl)-ethyl)-3-amino-propyl]-6,7-dimethoxy-1-oxo-1,2,3,4-tetrahydro-isoquinoline-hydrochloride Prepared from 2-(N-methyl-3-amino-propyl)-6,7-dimethoxy-1-oxo-1,2,3,4-tetrahydro-isoquinoline and 3-(2-chloro-ethyl)-indole analogously to Example 1.

Yield: 32% of theory,

Calculated: C 65.56 H 7.04 N 9.17 Cl 7.74. Found: C 65.38 H 6.93 N 9.01 Cl 7.97.

$R_f$ value: 0.45 (silica gel, methylene chloride/methanol=10/1 in an $NH_3$ atmosphere).

EXAMPLE 12

2-[N-Methyl-N-(3-(indol-3-yl)-propyl)-3-amino-propyl]-6,7-dimethoxy-1-oxo-1,2,3,4-tetrahydro-isoquinoline-hydrochloride Prepared from 2-(N-methyl-3-amino-propyl)-6,7-dimethoxy-1-oxo-1,2,3,4-tetrahydro-isoquinoline and 3-(3-methylsulphonyloxy-propyl)-indole analogously to Example 1.

Yield: 38% of theory,

Calculated: C 66.16 H 7.26 N 8.90 Cl 7.51. Found: C 65.98 H 7.56 N 8.85 Cl 7.54.

$R_f$ value: 0.34 (silica gel, methylene chloride/methanol=10/1 in an $NH_3$ atmosphere).

EXAMPLE 13

2-[N-Methyl-N-(4-(thien-2-yl)-butyl)-3-amino-propyl]-5,6-dimethoxy-phthalimide

Prepared from 2-(3-methylamino-propyl)-5,6-dimethoxy-phthalimide and 2-(4-bromo-butyl)-thiophene analogously to Example 1.

Yield: 80% of theory,

Calculated: C 63.44 H 6.78 N 6.73 S 7.70. Found: C 63.50 H 6.71 N 6.75 S 7.90.

$R_f$ value: 0.57 (silica gel, methylene chloride/methanol=9/1).

EXAMPLE 14

2-[N-Methyl-N-(3-(indol-3-yl)-propyl)-3-amino-propyl]-5,6-dimethoxy-phthalimide

Prepared from 2-(3-methylamino-propyl)-5,6-dimethoxy-phthalimide and 3-(3-methylsulphonyloxy-propyl)-indole analogously to Example 1.

Yield: 51% of theory,

Calculated: C 68.95 H 6.71 N 9.65. Found: C 69.20 H 6.78 N 9.60.

$R_f$ value: 0.36 (silica gel, methylene chloride/methanol=9/1).

EXAMPLE 15

2-[N-Methyl-N-(2-(thien-3-yl)-ethyl)-3-amino-propyl]-5,6-dimethoxy-phthalimide

Prepared from 2-(3-methylamino-propyl)-5,6-dimethoxy-phthalimide and 3-(2-bromo-butyl)-thiophene analogously to Example 1.

Yield: 73% of theory,

Calculated: C 61.84 H 6.23 N 7.21 S 8.25. Found: C 61.64 H 6.28 N 7.19 S 8.09.

$R_f$ value: 0.48 (silica gel, methylene chloride/methanol=9/1).

EXAMPLE 16

2-[N-Methyl-N-(2-(benzo[b]thien-3-yl)-ethyl)-3-amino-propyl]-5,6-dimethoxy-phthalimide Prepared from 2-(3-methylamino-propyl)-5,6-dimethoxy-phthalimide and 3-(2-methylsulphonyloxy-ethyl)-benzo[b]thiophene analogously to Example 1.

Yield: 41% of theory,

Calculated: C 65.73 H 5.98 N 6.39 S 7.31. Found: C 65.78 H 5.80 N 6.19 S 7.42.

$R_f$ value: 0.61 (silica gel, methylene chloride/methanol=9/1).

EXAMPLE 17

2-[N-Methyl-N-(2-(thien-2-yl)-ethyl)-3-amino-propyl]-5,6-dimethoxy-phthalimide

Prepared from 2-(3-methylamino-propyl)-5,6-dimethoxy-phthalimide and 3-(2-bromo-ethyl)-thiophene analogously to Example 1.

Yield: 44% of theory,

Calculated: C 61.84 H 6.23 N 7.21 S 8.25. Found: C 61.59 H 6.20 N 7.02 S 8.42.

$R_f$ value: 0.24 (silica gel, methylene chloride/methanol=9/1).

EXAMPLE 18

2-[N-Methyl-N-(3-(pyridin-3-yl)-propyl)-3-amino-propyl]-6,7-dimethoxy-1-oxo-1,2,3,4-tetrahydro-isoquinoline dihydrochloride-monohydrate Prepared from 2-(3-methylamino-propyl)-6,7-dimethoxy-1-oxo-1,2,3,4-tetrahydro-isoquinoline and 3-(3-chloro-propyl)-pyridine analogously to Example 1.

Yield: 31% of theory,

Calculated: C 56.55 H 7.22 N 8.60 Cl 14.51. Found: C 56.53 H 7.49 N 8.45 Cl 14.71.

$R_f$ value: 0.20 (silica gel, ethyl acetate/ethanol/ammonia=80/40/2).

EXAMPLE 19

2-[N-Methyl-N-(3-(pyridin-3-yl-N-oxide)-propyl)-3-amino-propyl]-6,7-dimethoxy-1-oxo-1,2,3,4-tetrahydro-isoquinoline dihydrochloride Prepared from 2-(3-methylamino-propyl)-6,7-dimethoxy-1-oxo-1,2,3,4-tetrahydro-isoquinoline and 3-(3-chloro-propyl)-pyridine-N-oxide analogously to Example 1.

Yield: 33% of theory,

Calculated: C 57.02 H 6.45 N 8.67 Cl 14.63. Found: C 57.07 H 6.23 N 8.44 Cl 14.57.

$R_f$ value: 0.35 (silica gel, ethyl acetate/ethanol/ammonia=50/45/5).

EXAMPLE 20

2-[N-Methyl-N-(2-(indol-3-yl)-ethyl)-3-amino-propyl]-5,6-dimethoxy-1,3-dihydro-1-oxo-isoindole hydrochloride Prepared from 2-[N-methyl-N-(2-(indol-3-yl)-ethyl)-3-amino-propyl]-5,6-dimethoxy-phthalimide analogously to Example 3.

Yield: 25% of theory,

Calculated: C 64.93 H 6.81 N 9.47 Cl 7.99. Found: C 64.80 H 6.81 N 9.41 Cl 8.03.

$R_f$ value: 0.29 (silica gel, methylene chloride/methanol=9/1).

EXAMPLE 21

2-[N-Methyl-N-(3-(indol-3-yl)-propyl)-3-amino-propyl]-5,6-dimethoxy-1,3-dihydro-1-oxo-isoindole hydrochloride Prepared from 2-[N-methyl-N-(3-(indol-3-yl)-propyl)-3-amino-propyl]-5,6-dimethoxy-phthalimide analogously to Example 3.

Yield: 24% of theory,

Calculated: C 65.56 H 7.04 N 9.18 Cl 7.74. Found: C 65.41 H 7.24 N 8.86 Cl 7.91.

$R_f$ value: 0.36 (silica gel, methylene chloride/methanol=6/4).

EXAMPLE 22

2-[N-Methyl-N-(2-(thien-3-yl)-ethyl)-3-amino-propyl]-5,6-dimethoxy-1,3-dihydro-1-oxo-isoindole dihydrochloride Prepared from 2-[N-methyl-N-(2-(thien-3-yl)-ethyl)-3-amino-propyl]-5,6-dimethoxy-phthalimide analogously to Example 3.

Yield: 70% of theory,

Melting point: 187°-188° C.

Calculated: C 53.69 H 6.31 N 6.30 Cl 15.85 S 7.16. Found: C 53.54 H 6.49 N 6.48 Cl 15.78 S 7.17.

$R_f$ value: 0.43 (silica gel, methylene chloride/methanol=9/1).

EXAMPLE 23

2-[N-Methyl-N-(2-(benzo[b]thien-3-yl)-ethyl)-3-amino-propyl]-5,6-dimethoxy-1,3-dihydro-1-oxo-isoindole dihydrochloride Prepared from 2-[N-methyl-N-(2-(benzo[b]thien-3-yl)-ethyl)-3-amino-propyl)-5,6-dimethoxy-phthalimide analogously to Example 3.

Yield: 63% of theory,

Calculated: C 57.94 H 6.08 N 5.63 Cl 14.25 S 6.44. Found: C 58.19 H 6.25 N 5.82 Cl 14.32 S 6.26.

$R_f$ value: 0.43 (silica gel, methylene chloride/methanol=9/1).

EXAMPLE 24

2-[N-Methyl-N-(3-(pyridin-4-yl)-propyl)-3-amino-propyl]-5,6-dimethyl-1,3-dihydro-1-oxo-isoindole Prepared from 2-[N-methyl-N-(3-(pyridin-4-yl)-propyl)-3-amino-propyl]-5,6-dimethyl-phthalimide analogously to Example 3.

Yield: 80% of theory,

Melting point: 82°-84° C.

Calculated: C 75.17 H 8.32 N 11.95. Found: C 74.98 H 8.39 N 11.76.

EXAMPLE 25

2-[N-Methyl-N-(3-(pyridin-3-yl)-propyl)-3-amino-propyl]-5,6-dimethoxy-1,3-dihydro-1-oxo-isoindole hydrochloride Prepared from 2-[N-methyl-N-(3-(pyridin-3-yl)-propyl)-3-amino-propyl]-5,6-dimethoxy-phthalimide analogously to Example 3.

Yield: 60% of theory,

Melting point: 180°-182° C.

Calculated: C 62.91 H 7.20 N 10.00 Cl 8.44. Found: C 62.75 H 7.09 N 9.85 Cl 8.14.

EXAMPLE 26

2-[N-Methyl-N-((pyridin-3-yl)-methyl)-3-amino-propyl]-5,6-dimethoxy-1,3-dihydro-1-oxo-isoindole dihydrochloride Prepared from 2-[N-methyl-N-((pyridin-3-yl)-methyl)-3-amino-propyl]-5,6-dimethoxy-phthalimide analogously to Example 3.

Yield: 72% of theory,

Calculated: C 56.07 H 6.35 N 9.81 Cl 16.55. Found: C 56.16 H 6.38 N 9.85 Cl 16.44.

$R_f$ value: 0.35 (silica gel, ethyl acetate/ethanol/ammonia=90/10/1).

EXAMPLE 27

2-[N-Methyl-N-(2-(6,7-dimethoxy-isoquinolin-4-yl)-ethyl)-3-amino-propyl]-5,6-dimethoxy-1,3-dihydro-1-oxo-isoindole hydrochloride Prepared from 2-[N-methyl-N-(2-(6,7-dimethoxy-isoquinolin-4-yl)-ethyl)-3-amino-propyl]-5,6-dimethoxy-phthalimide analogously to Example 3.

Yield: 90% of theory, Melting point: 202°-204° C.

Calculated: C 62.84 H 6.64 N 8.14 Cl 6.87. Found: C 62.61 H 6.78 N 7.95 Cl 6.59.

$R_f$ value: 0.50 (silica gel, ethyl acetate/ethanol/ammonia=50/45/5).

EXAMPLE 28

2-[N-Methyl-N-(2-(6,7-dimethoxy-isoquinolin-4-yl)-ethyl)-3-amino-propyl]-5,6-dimethyl-1,3-dihydro-1-oxo-isoindole hydrochloride-monohydrate Prepared from 2-[N-methyl-N-(2-(6,7-dimethoxy-isoquinolin-4-yl)-ethyl)-3-amino-propyl]-5,6-dimethoxy-phthalimide analogously to Example 3.

Yield: 81% of theory, Melting point: 227°-229° C.

Calculated: C 60.22 H 6.92 N 7.80 Cl 13.16. Found: C 60.40 H 7.03 N 8.05 Cl 13.08.

EXAMPLE 29

2-[N-Methyl-N-((pyridin-3-yl)-methyl)-3-amino-propyl]-5,6-dimethyl-1,3-dihydro-1-oxo-isoindole Prepared from 2-[N-methyl-N-((pyridin-3-yl)-methyl)-3-amino-propyl]-5,6-dimethoxy-phthalimide analogously to Example 3.

Yield: 73% of theory,

Melting point: 93°-95° C.

Calculated: C 74.27 H 7.79 N 12.99. Found: C 74.27 H 7.73 N 12.92.

EXAMPLE 30

2-[N-Methyl-N-((pyridin-3-yl)-methyl)-3-amino-propyl]-6,7-methylenedioxy-1-oxo-1,2,3,4-tetrahydro-isoquinoline hydrochloride Prepared from 2-(2-formyl-ethyl)-6,7-methylenedioxy-1-oxo-1,2,3,4-tetrahydro-isoquinoline and 3-(methylamino-methyl)-pyridine analogously to Example 4.

Yield: 83% of theory,

Melting point: 203°-205° C.

Calculated: C 61.61 H 6.20 N 10.79 Cl 9.09. Found: C 61.72 H 6.18 N 10.62 Cl 8.96.

EXAMPLE 31

2-[N-Methyl-N-((pyridin-3-yl)-methyl)-3-amino-propyl]-5,6-dimethyl-phthalimide

Prepared from 2-(2-formyl-ethyl)-5,6-dimethyl-phthalimide and 3-(methylamino-methyl)-pyridine analogously to Example 4.

Yield: 80% of theory,
Melting point: 71°–72° C.
Calculated: C 71.19 H 6.87 N 12.45. Found: C 70.98 H 6.77 N 12.32.

EXAMPLE 32

2-[N-Methyl-N-(3-(pyridin-4-yl)-propyl)-3-amino-propyl]-5,6-dimethyl-phthalimide dihydrochloride-hemihydrate Prepared from 2-(2-formyl-ethyl)-5,6-dimethyl-phthalimide and 4-(3-methylamino-methyl)-pyridine analogously to Example 4.

Yield: 68% of theory,
Calculated: C 59.05 H 6.76 N 9.39 Cl 15.84. Found: C 58.95 H 6.86 N 9.11 Cl 15.64.
$R_f$ value: 0.60 (silica gel, ethyl acetate/ethanol/ammonia=90/10/1).

EXAMPLE 33

2-[N-Methyl-N-(2-(6,7-dimethoxy-isoquinolin-4-yl)-ethyl)-3-amino-propyl]-5,6-dimethyl-phthalimide Prepared from 2-(2-formyl-ethyl)-5,6-dimethyl-phthalimide and 4-(2-methylamino-ethyl)-6,7-dimethoxy-isoquinoline analogously to Example 4.

Yield: 76% of theory,
Melting point: 122°–124° C.
Calculated: C 70.26 H 6.77 N 9.10. Found: C 70.43 H 6.85 N 8.98.

EXAMPLE 34

2-[N-Methyl-N-(2-(pyridin-2-yl)-ethyl)-3-amino-propyl]-5,6-dimethoxy-phthalimide Prepared from 2-(2-formyl-ethyl)-5,6-dimethoxy-phthalimide and 2-(2-methylamino-ethyl)-pyridine analogously to Example 4.

Yield: 63% of theory,
Melting point: 120°–122° C.
Calculated: C 65.78 H 6.58 N 10.96. Found: C 65.90 H 6.55 N 11.11.

EXAMPLE 35

2-[N-Methyl-N-(2-(6,7-dimethoxy-isoquinolin-4-yl)-ethyl)-3-amino-propyl]-5,6-dimethoxy-phthalimide hemihydrate Prepared from 2-(2-formyl-ethyl)-5,6-dimethoxy-phthalimide and 4-(2-methylamino-ethyl)-6,7-dimethoxy-isoquinoline analogously to Example 4.

Yield: 75% of theory,
Melting point: 158°–160° C.
Calculated: C 64.52 H 6.42 N 8.36. Found: C 64.44 H 6.46 N 8.44.

EXAMPLE 36

2-[N-Methyl-N-(2-(6,7-dimethoxy-isoquinolin-4-yl)-ethyl)-3-amino-propyl]-6,7-methylenedioxy-1-oxo-1,2,3,4-tetrahydro-isoquinoline dihydrochloride-hemihydrate Prepared from 2-(2-formyl-ethyl)-6,7-methylenedioxy-1-oxo-1,2,3,4-tetrahydro-isoquinoline and 4-(2-methylamino-ethyl)-6,7-dimethoxy-isoquinoline analogously to Example 4.

Yield: 77% of theory,
Calculated: C 57.96 H 6.12 N 7.51 Cl 12.67. Found: C 57.85 H 6.06 N 7.34 Cl 12.82. $R_f$ value: 0.25 (silica gel, ethyl acetate/ethanol/ammonia=80/40/2).

EXAMPLE 37

2-[N-Methyl-N-(2-(6,7-dimethoxy-isoquinolin-4-yl)-ethyl)-3-amino-propyl]-6,7-methylenedioxy-1,2,3,4-tetrahydro-isoquinoline trihydrochloride-dihydrate Prepared from 2-[N-methyl-N-(2-(6,7-dimethoxy-isoquinolin-4-yl)-ethyl)-3-amino-propyl]-6,7-methylenedioxy-1-oxo-1,2,3,4-tetrahydro-isoquinoline analogously to Example 5.

Yield: 83% of theory,
Calculated: C 53.24 H 6.62 N 6.90 Cl 17.46. Found: C 53.06 H 6.66 N 6.91 Cl 17.53. $R_f$ value: 0.15 (silica gel, methylene chloride/ethanol=4/1).

EXAMPLE 38

2-[N-Methyl-N-(3-(pyridin-4-yl)-propyl)-3-amino-propyl]-5,6-dimethoxy-1,3-dihydro-isoindole dihydrochloride-monohydrate Prepared from 2-[N-methyl-N-(3-(pyridin-4-yl)-propyl)-3-amino-propyl]-5,6-dimethoxy-1,3-dihydro-1-oxo-isoindole analogously to Example 5.

Yield: 55% of theory,
Melting point: 248°–250° C.
Calculated: C 57.38 H 7.66 N 9.12 Cl 15.40. Found: C 57.28 H 7.52 N 9.02 Cl 15.50.

EXAMPLE 39

2-[N-Methyl-N-(4-(thien-2-yl)-butyl)-3-amino-propyl]-5,6-dimethoxy-1,3-dihydro-1-oxo-isoindole hydrochloride Prepared from 2-[N-methyl-N-(4-(thien-2-yl)-butyl)-3-amino-propyl]-5,6-dimethoxy-phthalimide analogously to Example 3.

Yield: 30% of theory,
Melting point: 171°–172° C. (decomp.).
Calculated: C 60.19 H 7.12 N 6.38 Cl 8.08 S 7.30. Found: C 59.92 H 7.21 N 6.44 Cl 8.29 S 7.41.

EXAMPLE 40

2-[N-Methyl-N-(4-(thien-2-yl)-butyl)-3-amino-propyl]-6,7-dimethoxy-1-oxo-1,2,3,4-tetrahydro-isoquinoline hydrochloride 0.83 g (4.0 mmol) of 6,7-dimethoxy-1-oxo-1,2,3,4-tetrahydro-isoquinoline are dissolved in 15 ml of dimethylformamide and 0.49 g (4.4 mmol) of potassium tert-.butoxide are added with stirring. After the exothermic reaction has died away the potassium salt is precipitated. It is cooled to 0° C., 1.3 g (4.4 mmol) of N-methyl-N-(4-(thien-2-yl)-butyl)-3-amino-1-bromo-propane are added and the mixture is left to react at 0° C. for 4 hours. After decomposition with ice water, the mixture is extracted with ethyl acetate, the organic phase is washed with water, dried over magnesium sulphate, concentrated by evaporation and purified over a silica gel column. The free base thus obtained is dissolved in acetone and the hydrochloride is precipitated with ethereal hydrochloric acid.

Yield: 0.63 g (35% of theory),
Melting point: 116°–119° C. (decomp).

Calculated: C 60.98 H 7.34 N 6.18 Cl 7.83 S 7.08.
Found: C 61.15 H 7.38 N 6.08 Cl 7.68 S 6.97.

EXAMPLE 41

2-[N-Methyl-N-(2-(benzo[b]thien-3-yl)-ethyl)-3-amino-propyl]-6,7-dimethoxy-1-thioxo-1,2,3,4-tetrahydro-isoquinoline 1.7 g (3.9 mmol) of 2-[N-methyl-N-(2-(benzo[b]thien-3-yl)-ethyl)-3-amino-propyl]-6,7-dimethoxy-1-oxo-1,2,3,4-tetrahydro-isoquinoline and 0.57 g (2.0 mmol) of 2,4-bis-(methylthio)-1,3-dithia-2,4-diphosphetan-2,4-disulphide are suspended in 15 ml of toluene and refluxed for 2 hours. The mixture is then evaporated down in vacuo and purified over a silica gel column with methylene chloride and increasing amounts of methanol.

Yield: 0.99 g (56% of theory),
Calculated: C 66.06 H 6.65 N 6.16 Cl 14.08. Found: C 65.85 H 6.58 N 6.28 S 14.26.

$R_f$ value: 0.49 (silica gel, methylene chloride).

EXAMPLE I

Tablets containing 25 mg of
2-[N-methyl-N-(2-(thien-3-yl)-ethyl)-3-amino-propyl]-5,6-dimethoxy-1,3-dihydro-1-oxo-isoindole hydrochloride

| Composition: | |
|---|---|
| 1 tablet contains: | |
| Active substance | 25.0 mg |
| Corn starch | 57.0 mg |
| Lactose | 48.0 mg |
| Polyvinylpyrrolidone | 4.0 mg |
| Magnesium stearate | 1.0 mg |
| | 135.0 mg |

Method of Preparation

The active substance, corn starch, lactose and polyvinylpyrrolidone were mixed together and moistened with water. The moist mixture is pushed through a screen with a mesh size of 1.5 mm and dried at about 45° C. The dry granulate is passed through a 1.0 mm mesh screen and mixed with magnesium stearate. The final mixture is compressed in a tablet press with dies 7 mm in diameter provided with a dividing notch to form tablets. Weight of tablet: 135 mg.

EXAMPLE II

Coated tablets containing 20 mg of
2-[N-methyl-N-(2-(thien-3-yl)-ethyl)-3-amino-propyl]-5,6-dimethoxy-1,3-dihydro-1-oxo-isoindole hydrochloride

| 1 tablet core contains: | |
|---|---|
| Active substance | 20.0 mg |
| Corn starch | 41.5 mg |
| Lactose | 30.0 mg |
| Polyvinylpyrrolidone | 3.0 mg |
| Magnesium stearate | 0.5 mg |
| | 95.0 mg |

Method of Preparation

The active substance, corn starch, lactose and polyvinylpyrrolidone are throughly mixed and moistened with water. The moist mass is forced through a 1 mm screen, dried at about 45° C. and then the granulate is passed through the same screen. After magnesium stearate has been added, convex tablet cores with a diameter of 6 mm are compressed in a tablet making machine. The tablet cores thus produced are coated in known manner with a coating consisting essentially of sugar and talc. The finished coated tablets are polished with wax. Weight of coated tablet: 145 mg.

EXAMPLE III

Ampoules containing 50 mg of
2-[N-methyl-N-(2-(thien-3-yl)-ethyl)-3-amino-propyl]-5,6-dimethoxy-1,3-dihydro-1-oxo-isoindole hydrochloride

| 1 ampoule contains: | |
|---|---|
| Active substance | 50.0 mg |
| Sorbitol | 30.0 mg |
| Water for injections ad | 2.0 ml |

Method of Preparation

In a suitable mixing vessel the active substance is dissolved in water for injections and the solution is made isotonic with sorbitol. After being filtered through a diaphragm filter the solution is transferred under a current of $N_2$ into purified and sterilized ampoules and autoclaved for 20 minutes in a jet of steam.

EXAMPLE IV

Suppositories containing 30 mg of
2-[N-methyl-N-(2-(thien-3-yl)-ethyl)-3-amino-propyl]-5,6-dimethoxy-1,3-dihydro-1-oxo-isoindole hydrochloride

| 1 suppository contains: | |
|---|---|
| Active substance | 0.030 g |
| Hard fat (e.g. Witepsol H 19 and W 45) | 1.670 g |
| | 1.700 g |

Method of Preparation

The hard fat is melted. At 38° C. the ground active substance is homogeneously dispersed in the melt. It is cooled to 35° C. and poured into slightly chilled suppository moulds.

EXAMPLE V

Drops solution containing 20 mg of
2-[N-methyl-N-(2-(thien-3-yl)-ethyl)-3-amino-propyl]-5,6-dimethoxy-1,3-dihydro-1-oxo-isoindole hydrochloride

| 100 ml of solution contain: | |
|---|---|
| Active substance | 0.4 g |
| Hydroxyethylcellulose | 0.15 g |
| Tartaric acid | 0.1 g |
| Sorbitol solution with 70% dry matter | 30.0 g |
| Glycerol | 10.0 g |
| Benzoic acid | 0.15 g |
| Dist. water ad | 100 ml |

Method of Preparation

The distilled water is heated to 70° C. The hydroxyethylcellulose, benzoic acid and tartaric acid are dissolved therein with stirring. The mixture is cooled to ambient temperature and the glycerol and sorbitol solution are added with stirring. At ambient temperature the active substance is added and stirred until completely dissolved. The syrup is then evacuated of any air with stirring.

What is claimed is:

1. A heteroaromatic amine derivative of general formula

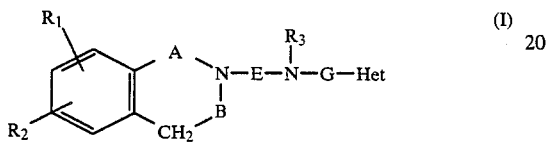
(I)

wherein

A is carbonyl or thiocarbonyl;

B is methylene;

E is straight-chained $C_2$–$C_4$ alkylene, which can be substituted by $C_1$–$C_3$ alkyl;

G is straight-chained $C_1$–$C_6$ akylene, which can be substituted by $C_1$–$C_3$ alkyl;

$R_1$ and $R_2$, which may be identical or different, are hydrogen, $C_1$–$C_3$ alkyl or $C_1$–$C_3$ alkoxy, $R_3$ is hydrogen, $C_3$–$C_5$ alkenyl, $C_1$–$C_3$ alkyl or $C_1$–$C_3$ phenylalkyl, and Het is benzo[b] thienyl group, whilst the carbon structure of the above-mentioned homocyclic or heteroaromatic ring may be mono-or di-substituted by halo, alkyl, hydroxy, alkoxy, phenylalkoxy, phenyl, dimethoxyphenyl, nitro, amino, acetylamino, carbamoylamino, N-alkyl-carbamnoyl-amino, hydroxymethyl, mercapto, alkyl mercapto, alkylsulphinyl, alkylsulphonyl, alkylsulphonyloxy, alkylsulphonylamino, alkoxycarbonylmethoxy, carboxymethoxy or alkoxymethyl group or may be substituted by a methylenedioxy or ethylenedioxy group, wherein the above-mentioned alkyl moieties may each contain from 1 to 3 carbon atoms, or an N-oxide, enantiomer, diastereomer or acid addition salt thereof.

2. The physiologically acceptable acid addition salt of the amine derivative as recited in claim 1.

3. An heteroaromatic amine derivative of general formula

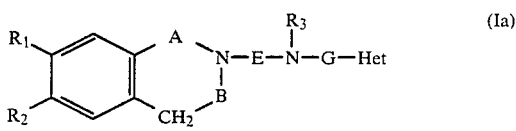
(Ia)

wherein

A is carbonyl or thiocarbonyl;

B is methylene;

E is n-propylene;

G is methylene, ethylene, n-propylene, n-butylene or n-pentylene;

$R_1$ and $R_2$, which may be identical or different, are hydrogen, methyl or methoxy, $R_3$ is hydrogen, methyl or allyl; and Het is a benzo[b]thien-2-yl, benzo[b]thien-3-yl, 6-hydroxy-benzo[b]thien-3-yl, 6-methoxy-benzo[b]-thien-3-yl, 5,6-dimethoxy-benzo[b]thien-3-yl, 2,5-dimethyl-benzo[b]thien-3-yl, 5-methoxy-benzo[b]-thien-2-yl, 6-methoxy-benzo[b]thien-2-yl, 6-methylmercapto-benzo[b]thien3-yl, 6-methylsulphinyl-benzo[b]thien-3-yl, 6-methylsulphonyl-benzo[b]thien-3-yl, 6-methylsulphonyloxy-benzo[b]-thien-3-yl, 6-carboxymethoxy-benzo[b]thien-3-yl, 6-dimethylamino-benzo[b]thien-3-yl, 6-methylsulphonylamino-benzo[b]thien-3-yl, 6-acetamino-benzo[b]thien-3-yl or benzo[b]thien-4-yl group.

or an enantiomer, diastereomer or acid addition salt thereof.

4. The physiologically acceptable acid·addition salt of the amine derivative as recited in claim 3.

5. The amine derivative as recited in claim 3 wherein $R_1$ and $R_2$, which may be identical or different, are methyl or methoxy;

$R_3$ is hydrogen or methyl, and

Het is a benzo[b]thien-2-yl or benzo[b]thien-3-yl group.

6. 2-[N-methyl-N-(2-(benzo[b]thien-3-yl)-ethyl)-3-amino-propyl]-6,7-dimethoxy-1-oxo-1,2,3,4-tetrahydro-isoquinoline or an acid addition salt thereof.

7. A composition of matter comprising an amine derivative as recited in claim 1 together with a pharmaceutically acceptable carrier.

8. A composition of matter comprising an amine derivative as recited in claim 3 together with a pharmaceutically acceptable carrier.

9. A method for treating cardiac insufficiency in a warm-blooded animal which comprises administering to said animal a therapeutically effective amount of an amine derivative as recited in claim 1.

10. A method for treating cardiac insufficiency in a warm-blooded animal which comprises administering to said animal a therapeutically effective amount of an amine derivative as recited in claim 3.

11. A method for treating ischaemic heart disease in a warm-blooded animal which comprises administering to said animal a therapeutically effective amount of an amine derivative as recited in claim 1.

12. A method for treating ischaemic heart disease in a warm-blooded animal which comprises administering to said animal a therapeutically effective amount of an amine derivative as recited in claim 3.

* * * * *